US011305080B2

(12) United States Patent
Nitta

(10) Patent No.: US 11,305,080 B2
(45) Date of Patent: Apr. 19, 2022

(54) RESPIRATORY ASSISTANCE DEVICE AND RESPIRATORY ASSISTANCE METHOD

(71) Applicant: METRAN CO., LTD., Kawaguchi (JP)

(72) Inventor: Kazufuku Nitta, Saitama (JP)

(73) Assignee: Metran Co., Ltd., Kawaguchi (JP)

( * ) Notice: Subject to any disclaimer, the term of this patent is extended or adjusted under 35 U.S.C. 154(b) by 358 days.

(21) Appl. No.: 16/336,310

(22) PCT Filed: Sep. 21, 2017

(86) PCT No.: PCT/JP2017/034099
§ 371 (c)(1),
(2) Date: Mar. 25, 2019

(87) PCT Pub. No.: WO2018/056356
PCT Pub. Date: Mar. 29, 2018

(65) Prior Publication Data
US 2020/0016353 A1     Jan. 16, 2020

(30) Foreign Application Priority Data

Sep. 26, 2016 (JP) .............................. JP2016-186415
Sep. 20, 2017 (JP) .............................. JP2017-179873

(51) Int. Cl.
*A61M 16/00* (2006.01)
*A61M 16/08* (2006.01)
(Continued)

(52) U.S. Cl.
CPC ...... *A61M 16/026* (2017.08); *A61M 16/0883* (2014.02); *A61M 16/1095* (2014.02);
(Continued)

(58) Field of Classification Search
CPC .............. A61M 16/00; A61M 16/0003; A61M 16/0057; A61M 16/0066; A61M 16/022;
(Continued)

(56) References Cited

U.S. PATENT DOCUMENTS 4,564,748 A   1/1986 Gupton
8,636,002 B2  1/2014 McAuley et al.
(Continued)

FOREIGN PATENT DOCUMENTS

CN    105749393 A   7/2016
GN    103974735 A   8/2014
(Continued)

OTHER PUBLICATIONS

Certification for Exception to Loss of Novelty filed in PCT/JP2017/034099; Publication: "The front line development of CPAP apparatus"; Publication date: Jul. 20, 2016; Publisher: Metran Co., Ltd. Tran Ngog Phuk (Kazuhuku Nitta).
(Continued)

*Primary Examiner* — Joseph D. Boecker
(74) *Attorney, Agent, or Firm* — Flynn Thiel, P.C.

(57) ABSTRACT

A respiratory assistance device including a respiratory interface device configured to be worn by a user and deliver a gas, a gas temperature measurement unit configured to measure a gas temperature that is a temperature of the gas, a warming unit configured to warm the gas, and a temperature change unit configured to change the gas temperature by controlling the warming unit. The respiratory assistance device can administer comfortable respiratory assistance even during sleep.

15 Claims, 18 Drawing Sheets

(51) Int. Cl.
*A61M 16/10* (2006.01)
*A61M 16/14* (2006.01)
*A61M 16/16* (2006.01)

(52) U.S. Cl.
CPC ........ *A61M 16/145* (2014.02); *A61M 16/161* (2014.02); *A61M 2205/3368* (2013.01); *A61M 2230/10* (2013.01); *A61M 2230/18* (2013.01); *A61M 2230/50* (2013.01); *A61M 2230/63* (2013.01)

(58) Field of Classification Search
CPC .. A61M 16/024; A61M 16/026; A61M 16/10; A61M 16/1075; A61M 16/109; A61M 16/1095; A61M 16/145; A61M 16/16; A61M 16/161; A61M 2230/18; A61M 2230/50; A61M 2230/63; A61F 2007/0006; A61F 2007/0017; A61G 11/00
See application file for complete search history.

(56) References Cited

U.S. PATENT DOCUMENTS

| | | | |
|---|---|---|---|
| 8,647,410 B2 | 2/2014 | Borenstein et al. | |
| 10,029,058 B2 | 7/2018 | Foote et al. | |
| 10,238,831 B2 | 3/2019 | Belson | |
| 2007/0208269 A1* | 9/2007 | Mumford | A61B 5/087 600/546 |
| 2008/0262377 A1* | 10/2008 | Belson | A61M 16/1075 600/549 |
| 2009/0126735 A1* | 5/2009 | Nitta | A61M 16/1075 128/203.26 |
| 2010/0132707 A1 | 6/2010 | Muller | |
| 2011/0125238 A1 | 5/2011 | Nofzinger | |
| 2011/0162647 A1* | 7/2011 | Huby | A61M 16/16 128/203.14 |
| 2012/0031405 A1* | 2/2012 | Geist | A61F 7/0085 128/204.15 |
| 2013/0066407 A1 | 3/2013 | Iiyama et al. | |
| 2013/0228181 A1 | 9/2013 | Ahmad et al. | |
| 2014/0144438 A1 | 5/2014 | Klasek | |
| 2014/0283829 A1* | 9/2014 | Miller | A61M 16/1095 128/203.14 |
| 2014/0338668 A1* | 11/2014 | Eum | A61M 16/0003 128/204.15 |
| 2015/0217079 A1* | 8/2015 | Mcauley | A61M 16/16 128/203.14 |
| 2016/0339201 A1 | 11/2016 | Nitta | |
| 2017/0136203 A1* | 5/2017 | Swain | A61M 16/0808 |
| 2018/0104426 A1* | 4/2018 | Oldfield | A61M 16/0666 |
| 2019/0183415 A1* | 6/2019 | Rytky | A61B 5/4857 |

FOREIGN PATENT DOCUMENTS

| | | |
|---|---|---|
| GN | 204193023 U | 3/2015 |
| JP | S59-151967 A | 8/1984 |
| JP | 2006-223332 A | 8/2006 |
| JP | 2010-501315 A | 1/2010 |
| JP | 2011-125618 A | 6/2011 |
| JP | 2013-518692 A | 5/2013 |
| JP | 2013-534461 A | 9/2013 |
| JP | 2014-083373 A | 5/2014 |
| JP | 2015-142646 A | 8/2015 |
| JP | 2016-501589 A | 1/2016 |
| JP | 2016-529069 A | 9/2016 |
| WO | 2005/070035 A2 | 8/2005 |
| WO | 2010/028427 A1 | 3/2010 |
| WO | 2011/156409 A1 | 12/2011 |
| WO | 2013/040198 A2 | 3/2013 |
| WO | 2016/042522 A1 | 3/2016 |

OTHER PUBLICATIONS

Website URL: http://www.terumo-taion.jp/health/sleep/01.html; date of retrieval: Sep. 7, 2016; Terumo Corporation.
International Search Report issued in PCT/JP2017/034099, dated Dec. 26, 2017.
Written Opinion issued in PCT/JP2017/034099, dated Dec. 26, 2017.
Japanese Office Action issued in corresponding Japanese Patent Application No. 2017-208957 dated Jul. 14, 2020 (5 pages).
Chinese Office Action issued in corresponding Chinese Application No. 201780059184.0 dated Feb. 26, 2021 (10 pages).
European Search Report issued in corresponding European Application No. 17853125.7 dated Apr. 23, 2020 (4 pages).
European Search Report issued in corresponding European Application No. 21177687.7, dated Sep. 10, 2021, received Sep. 7, 2021 (7 pages).

* cited by examiner

RESPIRATORY ASSISTANCE DEVICE AND RESPIRATORY ASSISTANCE METHOD

TECHNICAL FIELD

The present invention relates to a respiratory assistance device, such as an artificial respirator.

BACKGROUND ART

Automatic ventilation devices designed to be connected to the airway of a user (patient) and adjust or assist ventilation have been widely used in medical settings. Such devices are commonly referred to as artificial respirators. For example, a device (respiratory assistance device) designed to assist a patient's inhalation in synchronization with the patient's inhalation effort is a kind of artificial respirator. Among diseases to which more and more respiratory assistance devices have recently been applied in particular is sleep apnea syndrome (SAS). SAS occurs when airway muscles relax and the tongue root and the soft palate collapse to obstruct the airway during sleep. The number of potential SAS patients in Japan is said to be three million or more. SAS patients are considered to have a two to four times higher risk of developing a circulatory disease than healthy people. SAS patients are also likely to have a sleep disorder with a symptom of profound sleepiness, and have a risk of having a traffic accident twice as high as or higher than healthy people. For this kind of patient, continuous positive airway pressure therapy (CPAP) using a respiratory assistance device including a blower for applying a positive pressure to the airway (for example, see Japanese Patent Application Laid-Open No. 2015-142646) is considered to be effective. Such a respiratory assistance device blows compressed air supplied from the blower into the patient's airway.

FIG. 11 shows a configuration diagram of a conventional respiratory assistance device (CPAP) 301. A user 400 wears a respiratory interface device 410 such as a nasal mask for covering the nasal part. The respiratory interface device 410 is fixed to the head by a fixing tool. A positive pressure is continuously applied to the interior of the airway even during sleep, whereby the obstruction of the airway is prevented. The conventional respiratory assistance device 301 includes a blower 340 and a humidifying device 350. A gas is supplied through a respiratory circuit 370 and from the respiratory interface device 410 to the airway of the user 400. The gas is given moisture from the humidifying device 350, warmed by a warming unit 380 to prevent condensation, and then blown into the nasal part of the user 400. A typical artificial respirator has a similar basic structure, and how to control the temperature and humidity of the blown gas is an issue of extreme importance.

CITATION LIST

Patent Literature

Patent Literature 1: Japanese Patent Application Laid-Open No. 2015-142646

Non-Patent Literature

Non-Patent Literature 1: TERUMO CORPORATION, [online], [searched on Sep. 7, 2016], the Internet (URL: http://www.terumo-taion.jp/health/sleep/01.html)

SUMMARY OF INVENTION

Technical Problem

However, respiratory assistance devices used for respiratory assistance have been developed to date with emphasis on the function of resolving airway obstruction. Not much attention has been paid to improving the comfort of the user.

For example, a respiratory assistance device for providing respiratory assistance for CPAP typically blows a gas of constant temperature and humidity, often a gas having a Celsius temperature of 37° C. and a relative humidity of 100%. This simply follows the temperature and humidity of the gas blown from an artificial respirator during tracheal intubation, and due consideration has not been given to the comfort of the user.

FIG. 12 is a graph schematically showing a result of research by Uchiyama et al., cited in Non-Patent Literature 1 (TERUMO CORPORATION, [online], [searched on Sep. 7, 2016], the Internet (URL: http://www.terumo-taion.jp/health/sleep/01.html)). A region 510 shows a graph representing a relationship between time and core temperature. A region 520 shows a graph representing a relationship between time and a relative temperature of the back of the hands and feet to the body. A region 530 shows a graph representing a relationship between time and ease of sleep, in which greater values on the vertical axis indicate higher ease of sleep. A comparison between the regions 510 and 530 shows that the ease of sleep increases when the internal temperature of the body (core temperature) is low. The core temperature decreases during sleep, compared to during awakening. The ease of sleep (see the region 530) is found to peak at times when the core temperature is low, indicated by L1 to L3 in particular. Human lungs are considered to play a role like a radiator releasing heat inside the body to an outside environment through respiration. Blowing a high temperature gas into the airway during sleep is nothing but interfering with the body's attempt to lower the body temperature. The conventional respiratory assistance device is thus highly likely to hinder the user from having a good sleep. Possible reasons why nearly half of people using a respiratory assistance device for respiratory assistance quit using the respiratory assistance device within a year from start of use may include the difficulty in having a deep sleep, aside from device noise and poor usability.

In view of such circumstances, the present invention is directed to providing a respiratory assistance device that can administer comfortable respiratory assistance even during sleep.

Solution to Problem (1) The present invention provides a respiratory assistance device including: a respiratory interface device configured to be worn by a user and deliver a gas; a gas temperature measurement unit configured to measure a gas temperature that is a temperature of the gas; a warming unit configured to warm the gas; and a temperature change unit configured to change the gas temperature by controlling the warming unit.

According to the invention set forth in the above-described (1), the temperature change unit configured to change the gas temperature is included. The gas temperature can thus be changed to a temperature optimum for the user on a moment-to-moment basis during respiratory assistance, instead of simply blowing a gas of constant temperature.

According to the present invention, there is thus provided an excellent effect of improving comfort of the user.

(2) The present invention provides the respiratory assistance device set forth in the above-described (1), wherein the temperature change unit controls the warming unit to decrease the gas temperature after a lapse of a predetermined time from start of operation of the respiratory assistance device.

In providing respiratory assistance, blowing a warm gas before and after the start of sleep is comfortable to the user and often helps open the nasal cavity. Since, however, the core temperature decreases after the onset of sleep, the temperature of the blown gas is desirably decreased as well. According to the invention set forth in the above-described (2), there is provided an excellent effect that the gas is maintained at a constant temperature to improve the ventilation of the nasal cavity for a predetermined time from the start of operation of the respiratory assistance device, and then the warming unit is controlled to decrease the gas temperature to not interfere with a decrease in the core temperature of the user during sleep.

(3) The present invention provides the respiratory assistance device set forth in the above-described (1) or (2), further including a humidifying device configured to humidify the gas.

According to the invention set forth in the above-described (3), the respiratory assistance device further includes the humidifying device configured to humidify the gas. This provides an excellent effect that respiratory assistance can be provided without excessively drying the airway or the nasal cavity.

(4) The present invention provides the respiratory assistance device set forth in the above-described (3), wherein the humidifying device includes a water storage unit configured to store water intended for humidification and a porous hollow fiber unit to which the water in the water storage unit is supplied.

A humidifying device included in a conventional respiratory assistance device generates water vapor by boiling and evaporating water by heating with a heater. There has thus been a problem that the temperature of the blown gas is difficult to freely control. According to the humidifying device set forth in the above-described (4), the hollow fiber can draw up the water from the water storage unit by the capillary action. Since the hollow fiber has a porous surface, the water can transpire through the fine pores to humidify the blown gas. The inclusion of such a humidifying device in the respiratory assistance device enables humidification without heater-based heating. This provides an excellent effect of facilitating control on the gas temperature.

(5) The present invention provides the respiratory assistance device set forth in the above-described (3) or (4), including: a gas humidity measurement unit configured to measure a gas humidity that is a humidity of the gas; and a humidity change unit configured to control the humidifying device to change the gas humidity to a predetermined humidity.

According to the invention set forth in the above-described (5), the respiratory assistance device includes the gas humidity measurement unit configured to measure the humidity of the gas and the humidity change unit configured to change the gas humidity to a predetermined humidity. This provides an extremely excellent effect that a gas having a humidity optimum for the user can be blown.

(6) The present invention provides the respiratory assistance device set forth in the above-described (5), wherein the humidity change unit controls the humidifying device to supply a predetermined amount of water vapor on the basis of a correlation between the gas humidity and the gas temperature.

The amount of water vapor that can be contained in air depends on temperature. Then, the amount of water vapor optimum for the user also varies depending on the temperature of the gas blown by the respiratory assistance device. According to the invention set forth in the above-described (6), the humidity change unit can control the humidifying device to supply a predetermined amount of water vapor on the basis of the correlation between the gas humidity and the gas temperature. This provides an excellent effect of improving the comfort of the user.

(7) The present invention provides the respiratory assistance device set forth in the above-described (5) or (6), wherein the humidity change unit includes a timer processing unit configured to control the gas humidity according to a lapse of time.

According to the invention set forth in the above-described (7), the humidity change unit includes the timer processing unit configured to control the gas humidity according to a lapse of time. The gas humidity can thus be controlled according to a preset timer program. This facilitates providing the effect of improving the comfort of the user.

(8) The present invention provides the respiratory assistance device set forth in any one of the above-described 1 to 7, wherein the temperature change unit includes a timer processing unit configured to control the gas temperature according to a lapse of time.

According to the invention set forth in the above-described (8), the temperature change unit includes the timer processing unit configured to control the gas temperature according to a lapse of time. The gas temperature can thus be controlled according to a preset timer program. This facilitates providing the effect of improving the comfort of the user.

(9) The present invention provides the respiratory assistance device set forth in any one of the above-described (5) to (7), including a living body information acquisition unit configured to obtain living body information about the user, wherein the humidity change unit controls the humidifying device to change the gas humidity on the basis of the living body information.

According to the invention set forth in the above-described (9), a gas having a humidity optimum for the user can be blown on the basis of the living body information obtained by the living body information acquisition unit. This provides an excellent effect of improving the comfort of the user.

(10) The present invention provides the respiratory assistance device set forth in any one of the above-described (1) to (9), including a living body information acquisition unit configured to obtain living body information about the user, wherein the temperature change unit controls the warming unit to change the gas temperature on the basis of the living body information.

According to the invention set forth in the above-described (10), the living body information acquisition unit configured to obtain the living body information about the user is further included, and the temperature of the blown gas can be changed on the basis of the obtained information. A gas having a temperature optimum for the user can thus be blown, with an excellent effect of improving the comfort of the user.

(11) The present invention provides the respiratory assistance device set forth in either one of the above-described (9) and (10), wherein the living body information acquisition unit includes a core temperature measurement unit configured to measure a core temperature that is a temperature of a deep part of the user's living body.

According to the invention set forth in the above-described (11), the core temperature that is the temperature of the deep part of the user's living body can be measured. This provides an excellent effect that the core temperature during sleep can be measured to change the temperature of the gas according to a change therein.

(12) The present invention provides the respiratory assistance device set forth in the above-described (10), wherein the temperature change unit controls the warming unit to decrease the gas temperature when the core temperature measured by the core temperature measurement unit decreases.

It is commonly known that the core temperature decreases during sleep. Some search results suggest that promoting a decrease in the core temperature facilitates the onset of sleep. According to the invention set forth in the above-described (12), the warming unit can be controlled to decrease the blown gas temperature when the core temperature measured by the core temperature measurement unit decreases. This provides an excellent effect of improving the comfort of the user without interfering with sleep when providing respiratory assistance.

(13) The present invention provides the respiratory assistance device set forth in the above-described (11) or (12), wherein the temperature change unit controls the gas temperature to or below the core temperature.

According to the invention set forth in the above-described (13), the temperature of the gas blown by the respiratory assistance device can be controlled to or below the core temperature. The gas can thus be used to promote a decrease in the core temperature, with an excellent effect of facilitating the onset of sleep.

The present invention provides the respiratory assistance device set forth in any one of the above-described (9) to (13), wherein the living body information acquisition unit includes a body surface temperature measurement unit configured to measure a body surface temperature that is a temperature of a body surface of the user.

The body surface temperature that is the temperature of the human body surface is known to increase conversely while the core temperature decreases during sleep. The reason is considered to be that heat is released from the body surface to lower the core temperature. According to the invention set forth in the above-described (14), a unit configured to measure the body surface temperature are provided and the measurement result thereof is reflected on the temperature of the blown gas. This provides an excellent effect of enabling an improvement of the comfort of the user and an improvement of the sleep condition.

(15) The present invention provides the respiratory assistance device set forth in the above-described (14), wherein the temperature change unit controls the warming unit to decrease the gas temperature when the body surface temperature measured by the body surface temperature measurement unit increases.

As described above, the body surface temperature that is the temperature of the body surface is known to increase conversely while the core temperature decreases during sleep. According to the invention set forth in the above-described (15), the temperature change unit controls the warming unit to decrease the gas temperature when the body surface temperature of the user measured by the body surface temperature measurement unit increases. This provides an excellent effect that a comfortable respiratory assistance device having a high therapeutic effect for the user can be constructed.

(16) The present invention provides the respiratory assistance device set forth in any one of the above-described (1) to (15), further including an outside air temperature measurement unit configured to measure an outside air temperature that is a temperature of a place where the user is, wherein the temperature change unit controls the gas temperature on the basis of the outside air temperature.

Humans in sleep are considered to be conditioning their metabolic activities and the like so that a best sleep environment is achieved when they breathe at the temperature of the place of sleep (outside air temperature). With conventional respiratory assistance in which a gas heated by a heater-based heating humidifier device that comes with the respiratory assistance device is blown into the airway, the user sleeps with an excessive intake of heat energy and the sleep can be adversely affected. According to the invention set forth in the above-described (16), the outside air temperature measurement unit configured to measure the outside air temperature is included, and the temperature change unit determines the temperature of the blown gas on the basis of the outside air temperature. This provides an excellent effect that a gas having an optimum temperature can be blown during sleep.

(17) The present invention provides the respiratory assistance device set forth in the above-described (16), wherein the outside air temperature is defined as Tout (in units of degrees Celsius: ° C.), and the temperature change unit controls the gas temperature between (Tout-1) ° C. and (Tout-3) ° C.

Blowing a gas of excessively low temperature into the nasal cavity can cause nasal obstruction. According to the invention set forth in the above-described (15), the temperature change unit controls the temperature of the blown gas between (Tout-1) ° C. and (Tout-3) ° C. This provides an excellent effect that a gas of moderately low temperature can be blown, and both improved comfort of the user and therapeutic effect can be achieved in a compatible manner.

(18) The present invention provides the respiratory assistance device set forth in any one of the above-described (9) to (17), wherein the living body information acquisition unit includes a body movement measurement unit configured to measure body movement of the user.

Human sleep states are broadly divided between a deeply-sleeping "non-REM sleep" state and a lightly-sleeping "REM sleep" state. Body movement is known to decrease in the "non-REM sleep" state and increase in the "REM sleep" state. Which sleep state a person is in can be determined by detecting the body movement by using an acceleration sensor or the like. According to the invention set forth in the above-described (18), the respiratory assistance device can measure the body movement by using the body movement measurement unit, and blow a gas having a temperature and humidity adjusted to each sleep state. This provides an excellent effect that a respiratory assistance device conformable to the user can be constructed.

(19) The present invention provides the respiratory assistance device set forth in the above-described (18), including a sleep depth determination unit configured to determine depth of sleep of the user from the body movement measured by the body movement measurement unit, wherein the gas temperature is lowered when the depth of sleep increases.

In the "non-REM sleep" state which is a so-called deep sleep, the human core temperature decreases and breathing slows down. According to the invention set forth in the above-described (19), the respiratory assistance device includes the sleep depth determination unit configured to determine the depth of sleep of the user from the body movement, and the temperature of the gas can be lowered to decrease the core temperature in shifting to the "non-REM sleep" state which is a deep sleep. This provides an excellent effect that a respiratory assistance device comfortable to the user can be constructed.

(20) The present invention provides a respiratory assistance method including: a gas exchange step of delivering a gas to a user; a gas temperature measurement step of measuring a gas temperature that is temperature of the gas; a warming step of warming the gas; and a temperature change step of changing the gas temperature by controlling a warming unit.

According to the invention of the method set forth in the above-described (20), the temperature change step of changing the gas temperature is included. The gas temperature can thus be changed to a temperature optimum for the user on a moment-to-moment basis during respiratory assistance, instead of simply blowing a gas of constant temperature. According to the method of the present invention, an excellent effect of improving the comfort of the user is thus provided.

(21) The present invention provides the respiratory assistance device set forth in the above-described (1), including: the respiratory interface device configured to be worn by the user and deliver the gas; the gas temperature measurement unit configured to measure the gas temperature that is the temperature of the gas; the warming unit configured to warm the gas; the temperature change unit configured to change the gas temperature by controlling the warming unit; and a living body information acquisition unit configured to obtain living body information about the user, wherein the temperature change unit controls the warming unit to change the gas temperature on the basis of the living body information.

According to the invention set forth in the above-described (21), the living body information acquisition unit configured to obtain the living body information about the user is included, and the temperature of the blown gas can be changed on the basis of the obtained information. A gas having a temperature optimum for the user can thus be blown, with an excellent effect of improving the comfort of the user.

(22) The present invention provides the respiratory assistance device set forth in the above-described (21), further including a sleep level determination unit configured to determine a sleep level indicating a level of sleep of the user on the basis of the living body information obtained by the living body information acquisition unit, wherein the temperature change unit controls the warming unit to change the gas temperature on the basis of the sleep level.

According to the invention set forth in the above-described (22), the sleep level determination unit configured to determine the level of sleep of the user on the basis of the living body information obtained by the living body information acquisition unit is included. The temperature of the blown gas can thus be changed to a temperature suitable for the sleep level of the user, with an excellent effect of improving the comfort of the user.

(23) The present invention provides the respiratory assistance device set forth in the above-described (21) or the above-described (22), wherein the living body information acquisition unit includes a brain wave measurement unit configured to measure a brain wave of the user.

According to the invention set forth in the above-described (23), the living body information acquisition unit includes the brain wave measurement unit configured to measure the brain wave of the user. The temperature of the blown gas can thus be changed on the basis of the measured brain wave of the user. This provides an excellent effect of improving the comfort of the user.

(24) The present invention provides the respiratory assistance device set forth in the above-described (23), including a state determination unit configured to determine whether the user is in an awake state of being awake or in a sleep state of being asleep on the basis of the brain wave measured by the brain wave measurement unit.

The human core temperature typically decreases in a sleep state. Continuing blowing a gas having a temperature higher than a body surface temperature, for example, then interferes with the decrease in the core temperature. This is unpleasant for the user and can sometimes lower the quality of sleep. According to the invention set forth in the above-described (24), the state determination unit configured to determines whether the user is in an awake state or in a sleep state on the basis of the brain wave is included. If the user enters the sleep state, the temperature of the blown gas can thus be changed to a temperature suitable for the sleep state. This provides an excellent effect of improving the comfort of the user.

(25) The present invention provides the respiratory assistance device set forth in the above-described (23) or the above-described (24), including a brain wave determination unit configured to determine whether the user is in a REM sleep state or in a non-REM sleep state on the basis of the brain wave measured by the brain wave measurement unit.

Human sleep is classified into REM sleep and non-REM sleep on the basis of a difference in brain behavior. Sleep typically progresses from an onset to wake-up while repeating non-REM sleep and REM sleep alternately. The process of repetition and temporal changes in the core temperature correlate with each other. According to the invention set forth in the above-described (25), non-REM sleep and REM sleep can be determined from the measured brain wave, and thus the state of the core temperature can be estimated. This provides an excellent effect that the temperature of the blown gas can be changed to a temperature suitable for the user.

(26) The present invention provides the respiratory assistance device set forth in the above-described (25), wherein the temperature change unit controls the warming unit to increase or decrease the gas temperature on the basis of whether the user is in the REM sleep state or in the non-REM sleep state.

It is known that the human core temperature decreases as the sleep shifts from the first REM sleep after the onset of sleep to non-REM sleep, and the core temperature increases as the stage of non-REM sleep lightens. According to the invention set forth in the above-described (26), a change in the core temperature can be estimated on the basis of the brain wave, and thus the temperature of the blown gas can be changed to not interfere with a natural change in the core temperature. This provides an excellent effect that the comfort of the user can be improved.

(27) The present invention provides the respiratory assistance device set forth in the above-described (25) or the above-described (26), wherein if the brain wave determination unit determines that the user is in the non-REM sleep state, the temperature change unit controls the warming unit to decrease the gas temperature. Sleep typically progresses from an onset to wake-up while repeating non-REM sleep and REM sleep alternately. The process of repetition and temporal changes in the core temperature correlate with each other. Specifically, it is known that the core temperature tends to decrease as the sleep stage of non-REM sleep deepens, and the core temperature decreases in each of non-REM sleeps repeated several times before wake-up. According to the invention set forth in the above-described (27), the temperature change unit controls the warming unit to decrease the gas temperature if the user is determined to be in the non-REM sleep state. This provides an excellent effect that the temperature of the gas can be changed to not interfere with a natural change in the core temperature.

(28) The present invention provides the respiratory assistance device set forth in any one of the above-described (25) to (27), wherein the brain wave determination unit determines a degree of the non-REM sleep of the user, and the temperature change unit controls the warming unit to increase or decrease the gas temperature on the basis of the degree of the non-REM sleep.

The human core temperature tends to decrease when the degree of the non-REM sleep, or more specifically, the sleep stage of the non-REM sleep deepens, and be maintained when the degree of the non-REM sleep lightens. According to the invention set forth in the above-described (28), the brain wave determination unit that can determine the degree of the non-REM sleep is included. This provides an excellent effect that the temperature of the gas can be changed to not interfere with a natural change in the core temperature.

(29) The present invention provides the respiratory assistance device set forth in the above-described (1), wherein the temperature change unit further includes a timer processing unit configured to control the gas temperature according to a lapse of time.

According to the invention set forth in the above-described (29), the temperature change unit includes the timer processing unit configured to control the gas temperature according to a lapse of time. The gas temperature can thus be controlled according to a preset timer program. This facilitates providing the effect of improving the comfort of the user.

(30) The present invention provides the respiratory assistance device set forth in the above-described (29), wherein the timer processing unit performs control to maintain the temperature of the gas at or above a body surface temperature of the user for a predetermined time after the user starts running the device.

If the gas is blown through the nasal cavity, a gas temperature somewhat higher than the body surface temperature can help open the nasal cavity in an awake state. According to the invention set forth in the above-described (30), the temperature of the blown gas is maintained at or above the body surface temperature for an average time the user is considered to take from the start of operation of the device to the onset of sleep, such as 30 minutes. This provides an excellent effect that the nasal cavity can be opened to bring about a state in which the user can easily fall asleep.

(31) The present invention provides the respiratory assistance device set forth in the above-described (29) or the above-described (30), wherein the timer processing unit stops the warming unit.

The human core temperature typically decreases if an awake state shifts to a sleep state. Continuing blowing a gas having a temperature higher than the body surface temperature, for example, then interferes with the decrease in the core temperature. This is unpleasant for the user and can sometimes lower the quality of sleep. According to the invention set forth in the above-described (31), the warming of the gas can be automatically stopped after a lapse of an average time the user is considered to take from the start of operation of the device to the onset of sleep, such as 30 minutes. The temperature of the gas can thus be lowered to at least room temperature to not interfere with a natural change in the core temperature. This provides an excellent effect that the comfort of the user can be improved.

(32) The present invention provides the respiratory assistance device set forth in the above-described (29) or the above-described (30), wherein the timer processing unit controls the temperature of the gas to or below a body surface temperature of the user.

The human core temperature typically decreases if an awake state shifts to a sleep state. Continuing blowing a gas having a temperature higher than the body surface temperature, for example, then interferes with the decrease in the core temperature. This is unpleasant for the user and can sometimes lower the quality of sleep. According to the invention set forth in the above-described (32), the temperature of the blown gas can be automatically made lower than the body surface temperature according to a lapse of time. The temperature of the gas can thus be lowered to at least to room temperature to not interfere with a natural change in the core temperature. This provides an excellent effect that the comfort of the user can be improved.

(33) The present invention provides the respiratory assistance device set forth in the above-described (32), wherein the timer processing unit controls the temperature of the gas to a temperature higher than the melting point of water in an environment in which the device is run.

The device is intended for a user who does not have much trouble other than in the respiratory system. Lowering the temperature of the blown gas more than needed rather impairs the comfort of the user. According to the invention set forth in the above-described (33), the temperature of the blown gas is maintained at a temperature higher than the freezing point of water, or more specifically, the melting point of water in the environment in which the device is run. This provides an excellent effect that the comfort of the user is less likely to be impaired since an unnecessarily cold gas will not be blown.

(34) The present invention provides the respiratory assistance device set forth in any one of the above-described (29) to (33), wherein the timer processing unit performs control so that an increase region for increasing the temperature of the gas, a decrease region for decreasing the temperature of the gas, and a maintenance region for maintaining the temperature of the gas at a constant temperature are included according to predetermined order and time intervals input in advance.

The human core temperature changes with a lapse of time from the onset of sleep to wake-up. According to the invention set forth in the above-described (34), the temperature of the blown gas can be changed according to the predetermined order and time intervals input in advance. The gas can thus be blown at an optimum gas temperature according to an expected temporal change in the core temperature, with an excellent effect that the comfort of the user can be improved.

(35) The present invention provides a method for controlling a respiratory assistance device configured to deliver a gas to a user during sleep, the method including: a gas temperature measurement step in which the respiratory assistance device measures a gas temperature that is a temperature of the gas; a warming step in which the respiratory assistance device warms the gas; a temperature change step in which the respiratory assistance device changes the gas temperature by controlling a warming unit; and a living body information acquisition step in which the respiratory assistance device obtains living body information about the user, wherein the temperature change step by the respiratory assistance device includes performing control to modify the warming step to change the temperature gas on the basis of the living body information during sleep.

According to the invention set forth in the above-described (35), the living body information acquisition step of obtaining the living body information about the user is included. The temperature of the blown gas can be changed on the basis of the obtained information. A gas having a temperature optimum for the user can thus be blown, with an excellent effect of improving the comfort of the user.

(36) The present invention provides a method for controlling a respiratory assistance device configured to deliver a gas to a user during sleep, the method including: a gas temperature measurement step in which the respiratory assistance device measures a gas temperature that is a temperature of the gas; a warming step in which the respiratory assistance device warms the gas; and a temperature change step in which the respiratory assistance device changes the gas temperature by controlling a warming unit, wherein the temperature change step by the respiratory assistance device further includes a timer processing step of modifying the warming step to control the gas temperature according to a lapse of time.

According to the invention set forth in the above-described (36), the temperature change step includes the timer processing step of controlling the gas temperature according to a lapse of time. The gas temperature can thus be controlled according to a preset timer program. This facilitates providing the effect of improving the comfort of the user.

Advantageous Effects of Invention

According to the present invention, the living body information acquisition unit configured to obtain the living body information about the user is included, and the temperature of the blown gas can be changed on the basis of the obtained information. A gas having a temperature optimum for the user can thus be blown, with an excellent effect of improving the comfort of the user.

Moreover, according to the present invention, the temperature change unit includes the timer processing unit configured to control the gas temperature according to a lapse of time. The gas temperature can thus be controlled according to a preset timer program. This facilitates providing the effect of improving the comfort of the user.

DESCRIPTION OF EMBODIMENTS

Figure 1:
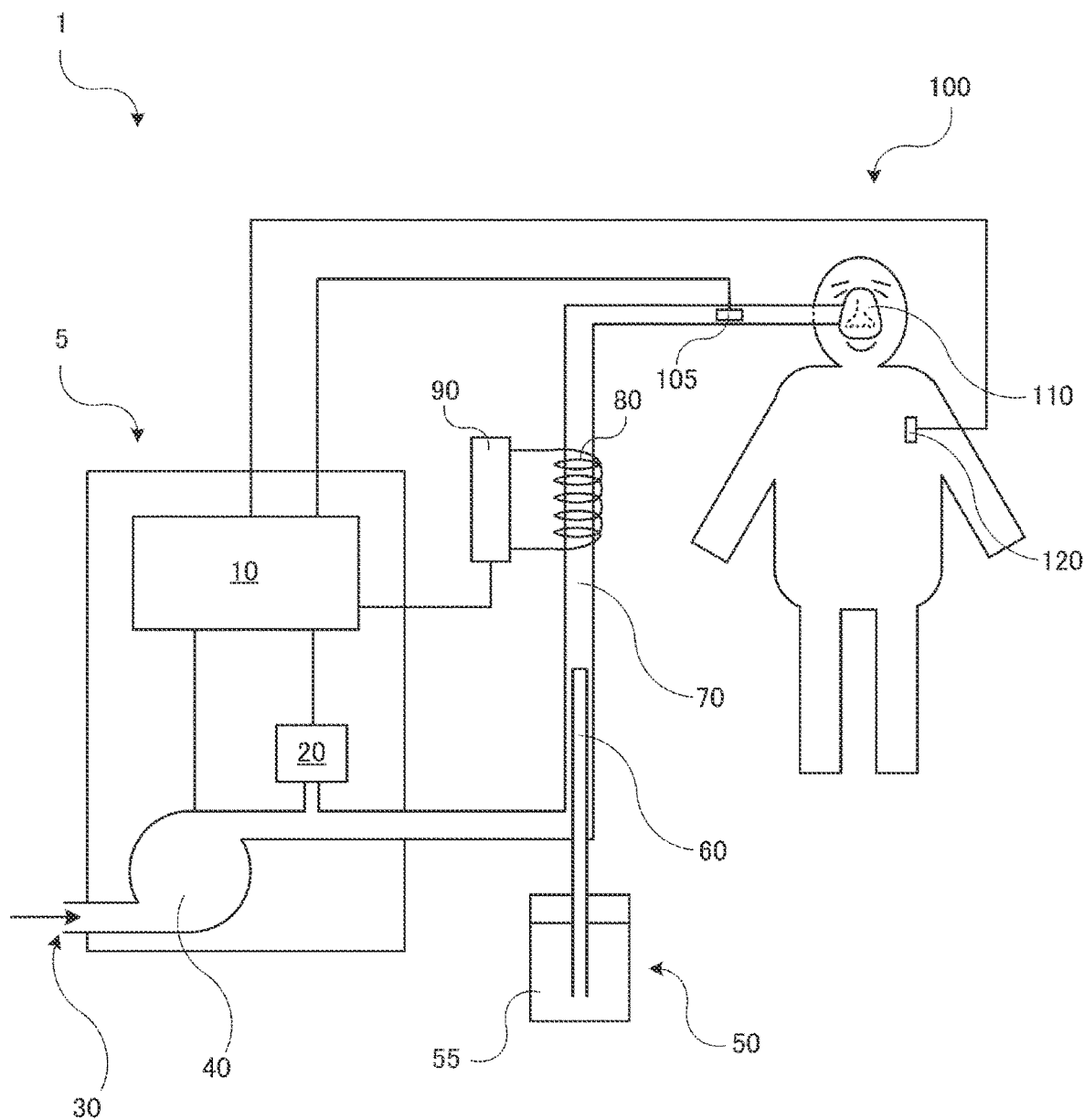
FIG. 1 shows an explanatory diagram of a respiratory assistance device according to a first embodiment of the present invention.

Embodiments of the present invention will be described below with reference to the accompanying drawings. FIGS. 1 to 17 show an example of implementation mode of the invention. In the diagrams, portions designated by the same reference numerals represent the same components. In the diagrams, some components are omitted as appropriate for simplification. Members are expressed in exaggerated sizes, shapes, thicknesses, or the like as appropriate.

FIG. 1 is an explanatory diagram for describing a respiratory assistance device 1 according to a first embodiment of the present invention. The respiratory assistance device 1 includes a main body 5, a humidifying device 50 which humidifies a gas to be blown, a respiratory circuit 70 including a duct for conveying the gas to be blown, a warming unit 80 which warms the gas in the respiratory circuit, a respiratory interface device 110 which is worn by a user and delivers the gas, and a core temperature measurement sensor 120 which detects a core temperature that is the temperature of a deep part of the user's living body. The respiratory interface device 110 desirably is a nasal mask or nasal prongs. To prevent difficulty in breathing out due to high pressure from expiration, a so-called relief valve, which opens to the air at increased pressure, is desirably provided on or near the respiratory interface device 110.

The main body 5 includes a blower 40 which blows a compressed gas, a flow rate measurement device 20 which measures the flow rate of the blown gas, and a control device 10 which controls the flow rate, pressure, and temperature of the gas. The blower 40 takes in the outside air from an intake port 30, and compresses and sends out the air to the respiratory circuit 70. The flow rate measurement device 20 here measures the flow rate of the blown gas, and the control device 10 performs control to achieve a prescribed pressure prescribed by a doctor. A pressure gauge for measuring the pressure of the blown gas is desirably provided.

The respiratory interface device 110 is connected to the respiratory circuit 70. A positive pressure gas is applied from the respiratory interface device 110 to the nasal cavity of a user 100. The respiratory circuit 70 or the respiratory interface device 110 includes a gas temperature sensor 105 which detects a gas temperature that is the temperature of the gas near the respiratory interface device 110. The warming unit 80 is provided on at least part of the respiratory circuit 70. The control device 10 controls a heater power supply 90 to control the gas temperature.

The humidifying device 50 is connected to the main body 5 or the respiratory circuit 70, and humidifies the gas to be blown to the user. The humidifying device 50 includes a water storage unit 55 which stores water intended for humidification, and a porous hollow fiber unit 60 to which the water in the water storage unit 55 is supplied. The porous hollow fiber unit 60 is inserted into the respiratory circuit 70, and transpires water vapor into the gas in the respiratory circuit 70 for humidification.

The core temperature measurement sensor 120 may be of zero heat flux type or of a type including a plurality of heat flux sensors.

Figure 2:
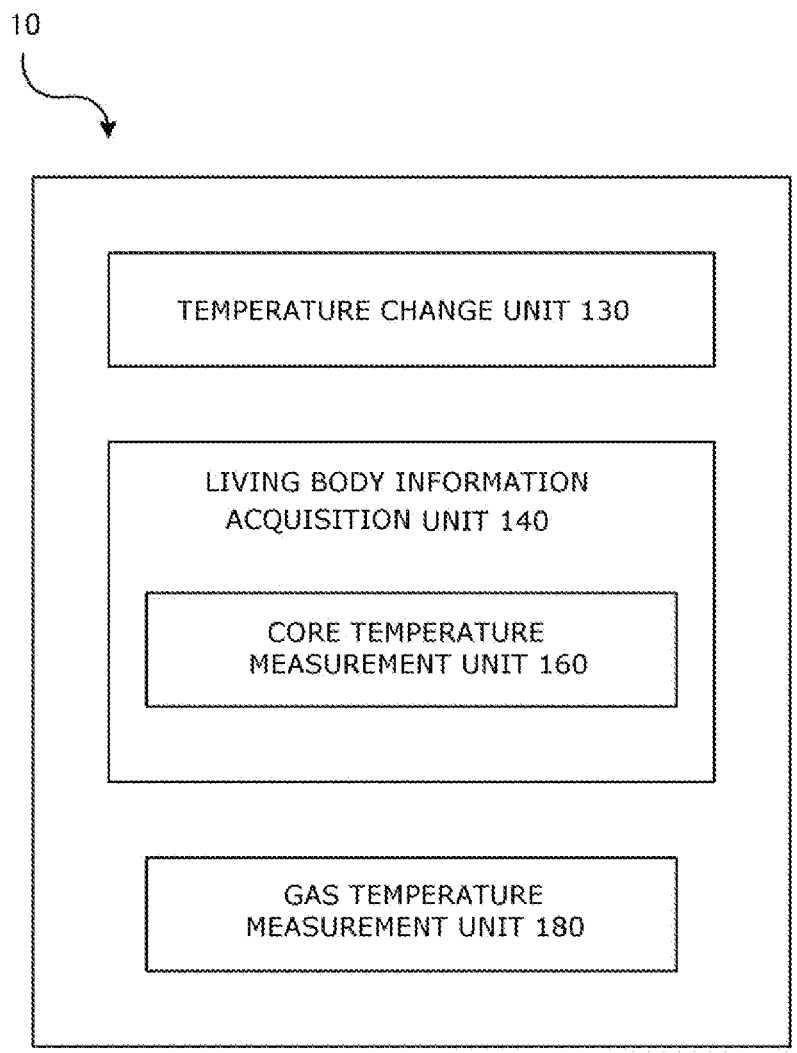
FIG. 2 is a block diagram of a control device that controls the respiratory assistance device.

FIG. 2 shows a block diagram of the control device 10. The control device 10 includes a living body information acquisition unit 140 which obtains living body information about the user, a temperature change unit 130 which changes the gas temperature by controlling the warming unit 80, and a gas temperature measurement unit 180 which measures the gas temperature. The living body information acquisition unit 140 includes a core temperature measurement unit 160 which measures the core temperature (see FIG. 1). The temperature change unit 130 is connected to the heater power supply 90. The core temperature measurement unit 160 is connected to the core temperature measurement sensor 120 (see FIG. 1). The temperature change unit 130 performs temperature control on the warming unit 80 to change the gas temperature on the basis of the core temperature that is living body information as will be described later. The gas temperature measurement unit 180 is connected to the gas temperature sensor 105 and measures the temperature of the gas (see FIG. 1). The control device 10 here desirably performs feedback control (such as PID control) on the warming unit 80 on the basis of the temperature of the gas obtained by the gas temperature measurement unit 180.

The control device 10 includes a CPU, a RAM, and a ROM, and performs various types of control. The CPU is a so-called central processing unit, and implements various functions by executing various programs. The RAM is used as a work area and storage area of the CPU. The ROM stores an operating system and programs to be executed by the CPU.

Figure 3A:
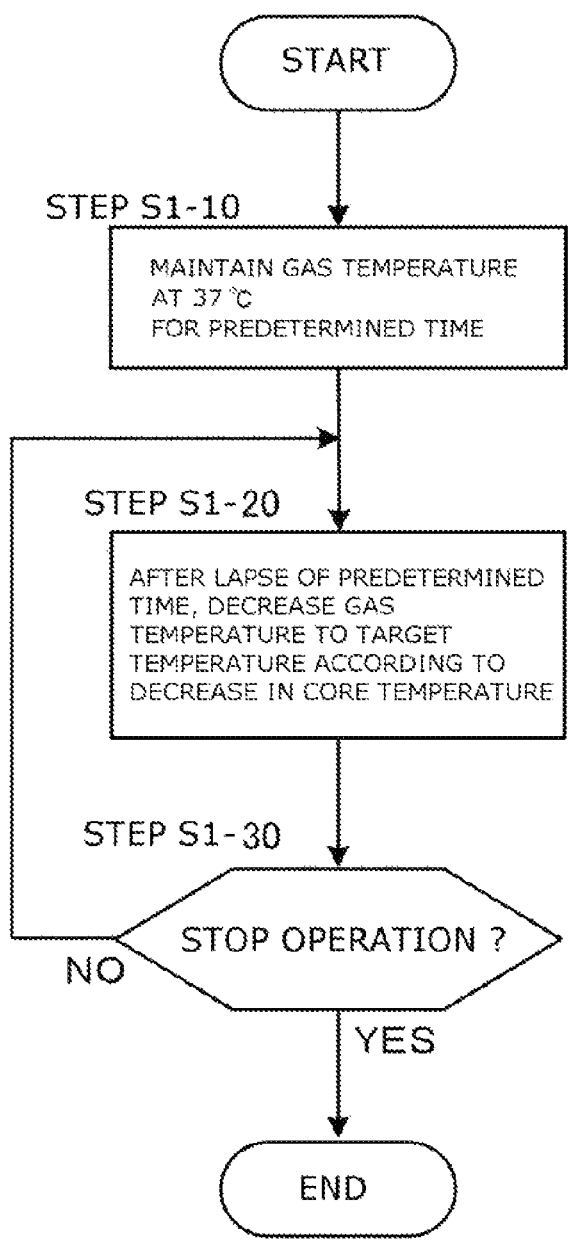
FIG. 3A is a flowchart about temperature control on a blown gas.

FIG. 3A shows a flowchart about the temperature control on the gas temperature, performed by the control device 10.

Initially, when the respiratory assistance device 1 is powered on, the blower 40 starts operation to start respiratory assistance (see FIG. 1). Although not shown in the drawings, setting values (such as a prescribed pressure) immediately before the previous power-off are automatically reflected upon power-on.

A timer function (not shown) for measuring an operation time from the start of operation is activated, and the gas temperature is maintained at a predetermined temperature, such as 37° C., for a predetermined time, such as 30 minutes (step S1-10). The reason is that blowing a relatively warm gas helps open the nasal cavity and is comfortable to the user during sleep onset. The predetermined time and the predetermined temperature are desirably adjustable as appropriate by the user.

If the user enters a sleep state after a lapse of the predetermined time from the start of operation of the respiratory assistance device 1, the user's core temperature detected by the core temperature measurement sensor 120 and measured by the core temperature measurement unit 160 starts to decrease. The temperature change unit 130 of the control device 10 controls the heater power supply 90 to decrease the temperature of the warming unit 80 accordingly, whereby the gas temperature is lowered to a predetermined target temperature (step S1-20). The target temperature is lower than the core temperature and desirably the same as the outside air temperature or desirably 1° C. to 3° C. lower than the outside air temperature. If the target temperature is substantially the same as the outside air temperature, the temperature change unit 130 can reduce the power supplied to the heater power supply 90 or set the power to zero.

To make the temperature of the gas lower than the outside air temperature, a cooling mechanism is desirably provided. The cooling mechanism may be one commonly used for gas cooling. Like an ordinary refrigerator, a refrigerant and a compressor may be used to draw the heat of vaporization from the gas for cooling. A Peltier device may be used. The humidifying device 50 itself can be used for cooling.

The target temperature desirably is adjustable by the user himself/herself during operation.

More specifically, the control device 10 controls the warming unit 80 to decrease the gas temperature on the basis of living body information that is the core temperature. The human core temperature typically decreases during sleep until immediately before awakening. The control device 10 therefore desirably controls the warming unit 80 to decrease the gas temperature when the core temperature measured by the core temperature measurement unit 160 decreases. The control device 10 here desirably performs feedback control on the warming unit 80 to achieve the target temperature by using the gas temperature detected by the gas temperature sensor 105 and measured by the gas temperature measurement unit 180.

The control device 10 then maintains the gas temperature at the target temperature and continues respiratory assistance (NO in step S1-30) until the user enters an awake state and turns off the power supply of the respiratory assistance device 1 to stop operation. If the respiratory assistance device 1 is powered off to stop operation, the control on the gas temperature is stopped at the same time (YES in step S1-30).

By the above-described operation, the respiratory assistance device 1 can control the warming unit 80 to decrease the temperature of the blown gas without interfering with a decrease in the core temperature during sleep. This enables respiratory assistance without interfering with sleep, and an excellent effect of improving the comfort of the user is provided. It will be understood that sleep comfort with artificial respiration also improves.

Figure 3B:
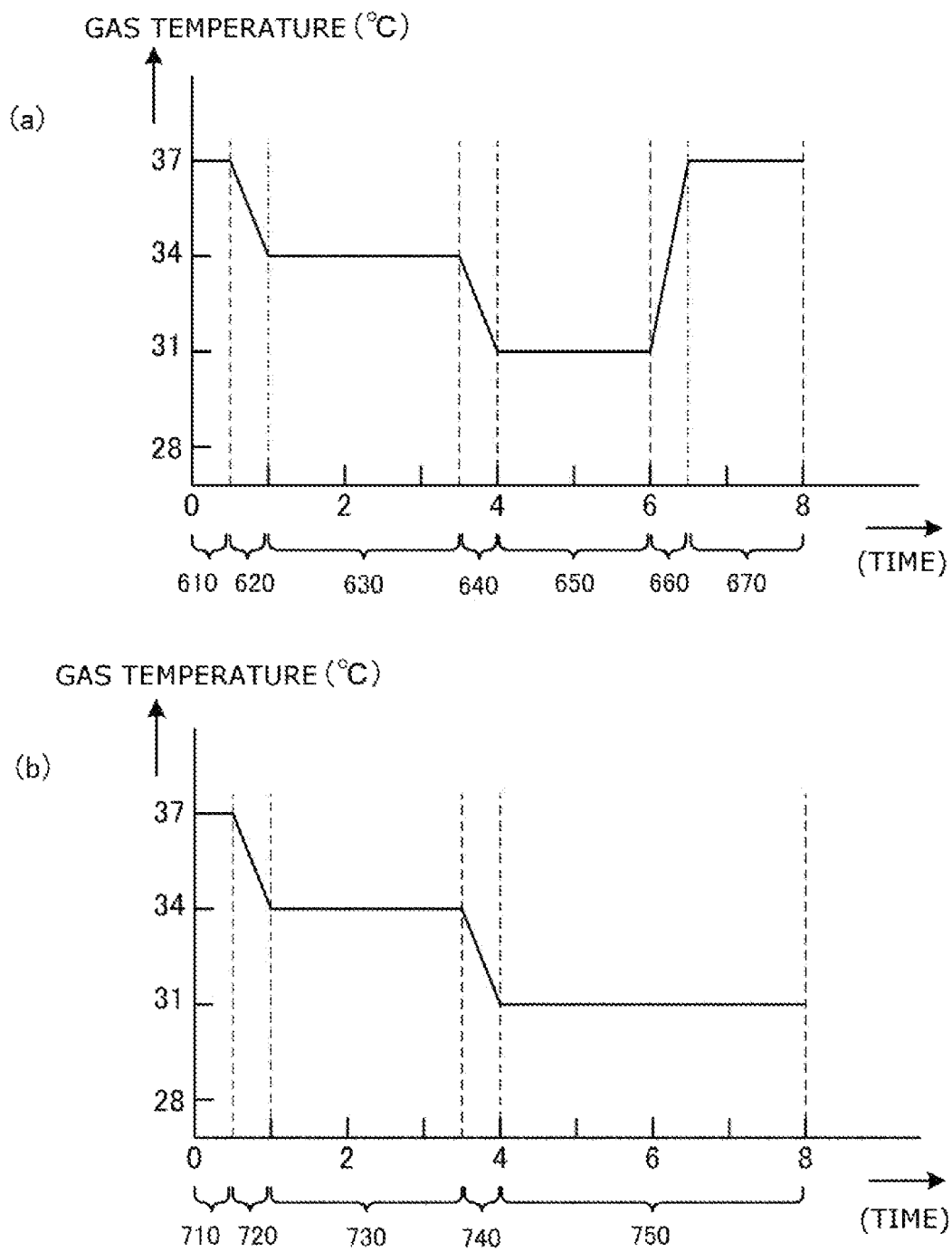
FIG. 3B shows graphs showing examples of the gas temperature control.

FIG. 3B shows graphs showing modified examples of gas temperature control.

FIG. 3B(a) shows an example in which the temperature change unit 130 (see FIG. 2) changes the gas temperature according to a timer (not shown) included in the respiratory assistance device 1 without using the living body information. A period 610 represents 30 minutes from the start of operation, during which the gas temperature is maintained at 37° C., for example. In a period 620, the gas temperature is lowered by 3° C. The gas temperature is maintained at 34° C. over the next two hours and thirty minutes (period 630). The gas temperature is then lowered further by 3° C. (period 640). The gas temperature is maintained at 31° C. over the next two hours (period 650). In a period 660 temporally approaching awakening, the temperature is increased by 6° C. The temperature is then maintained at 37° C. (period 670). Such timer operations can easily provide comfort during sleep for the user.

FIG. 3B(b) shows a case where the core temperature is measured and the target temperature is lowered to decrease the gas temperature according to a decrease in the core temperature. In the present modified example, the gas temperature is maintained at, for example, 37° C. for 30 minutes from the start of operation. The gas temperature is then lowered according to a decrease in the core temperature detected by the core temperature measurement sensor 120 and measured by the core temperature measurement unit 160.

Specifically, an operation for measuring the core temperature at predetermined regular time intervals and determining the target temperature accordingly as needed is performed (see FIG. 3A). In FIG. 3B(b), for example, the target temperature is changed as much as a temperature determined by multiplying a temporal change in the core temperature by a predetermined coefficient, e.g., 2.0 with reference to a temperature of 34° C. that is 2° C. lower than a typical human average body temperature of 36° C. More specifically, in a period 740, the gas temperature is lowered by 3° C. to follow a decrease of 1.5° C. in the core temperature. During a period 750 where the core temperature does not vary, the target temperature is determined so that the gas temperature is maintained at 31° C. To smoothly change the gas temperature for the sake of preventing an abrupt change in the gas temperature from stimulating the nasal cavity and interfering with the user's deep sleep, the target temperature may be determined by using a function such that a temperature change determined by the core temperature and time is small and temporally smooth. It will be understood that the temperature change unit 130 may be prepared with a lookup table of core temperatures and target temperatures in advance, and determine the target temperature on the basis of the core temperature measured by the core temperature measurement unit 160.

Note that in this modified example, an increase in the core temperature which often occurs upon awakening is not reflected on the gas temperature.

It will be understood that the gas temperature control according to the modified examples shown in FIGS. 3B(a) and 3B(b) described above are also applicable to other embodiments.

Figure 4:
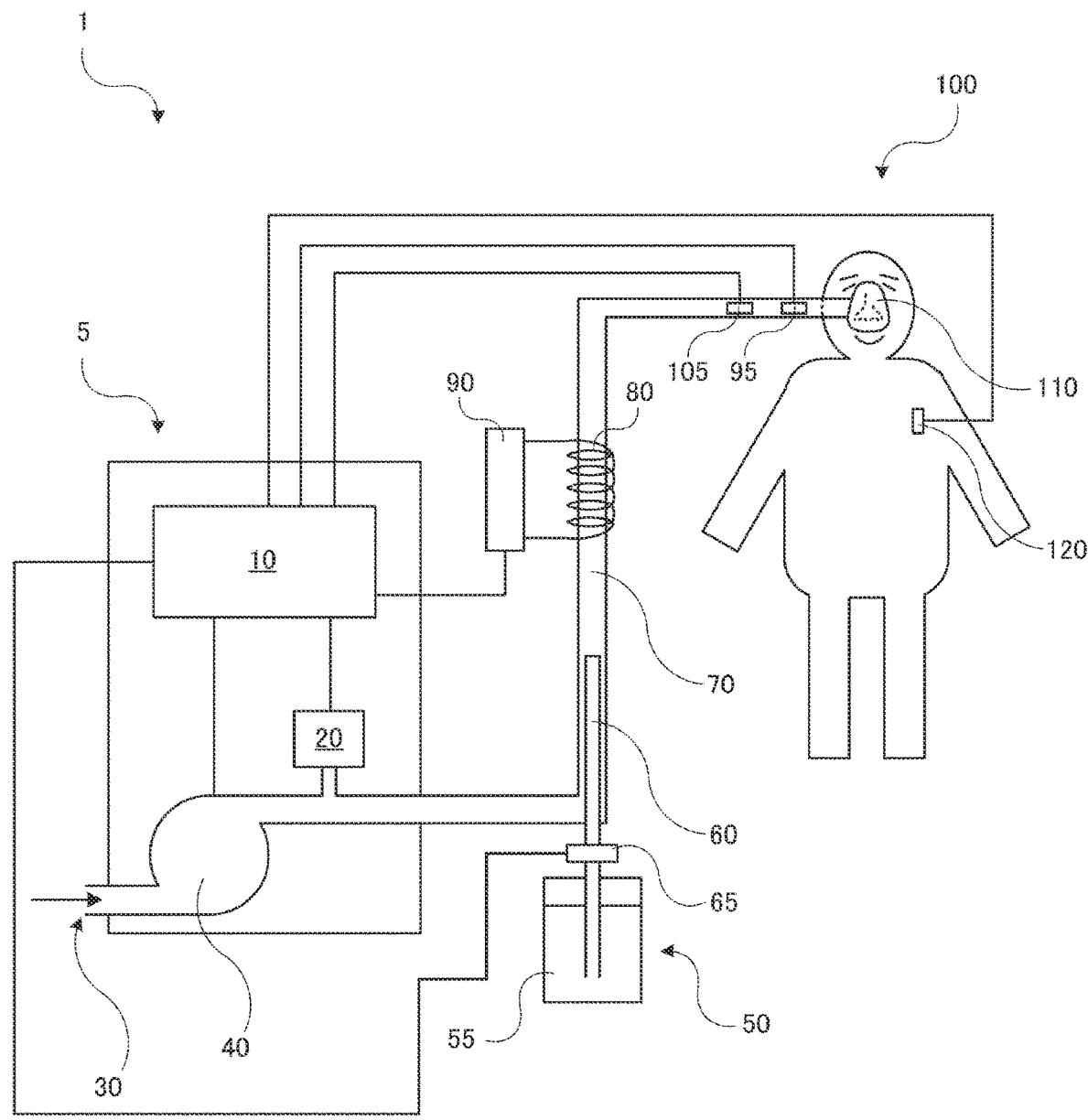
FIG. 4 is an explanatory diagram showing a respiratory assistance device according to a second embodiment of the present invention.

FIG. 4 shows an explanatory diagram of a respiratory assistance device 1 according to a second embodiment of the present invention. Differences from the first embodiment lie in a gas humidity sensor 95 which detects the humidity of the gas, and a humidity adjustment unit 65 which adjusts the amount of water vapor supplied from the humidifying device 50 to change humidity.

As a specific mechanism of the humidity adjustment unit 65 for adjusting humidity, the amount of water supplied to the porous hollow fiber unit 60 may be adjusted by a solenoid valve. The porous hollow fiber unit 60 may be provided with a heating unit, and the amount of heating may be adjusted to increase or decrease the amount of water vapor generated.

A conventional respiratory assistance device used for respiratory assistance blows a gas having a relative humidity of 100% from the air path. Whether the user is comfortable with such a gas depends on the situation. For example, the user under CPAP treatment has a self-humidification ability since the gas is blown through the nasal cavity capable of moistening the gas by itself. Then, in the second embodiment of the present invention, the humidity of the blown gas is maintained at a target humidity, for example, any value between 60% and 80% in relative humidity to promote the user's comfortable sleep. The target humidity is desirably adjustable by the user while the respiratory assistance device 1 is running.

Figure 5:
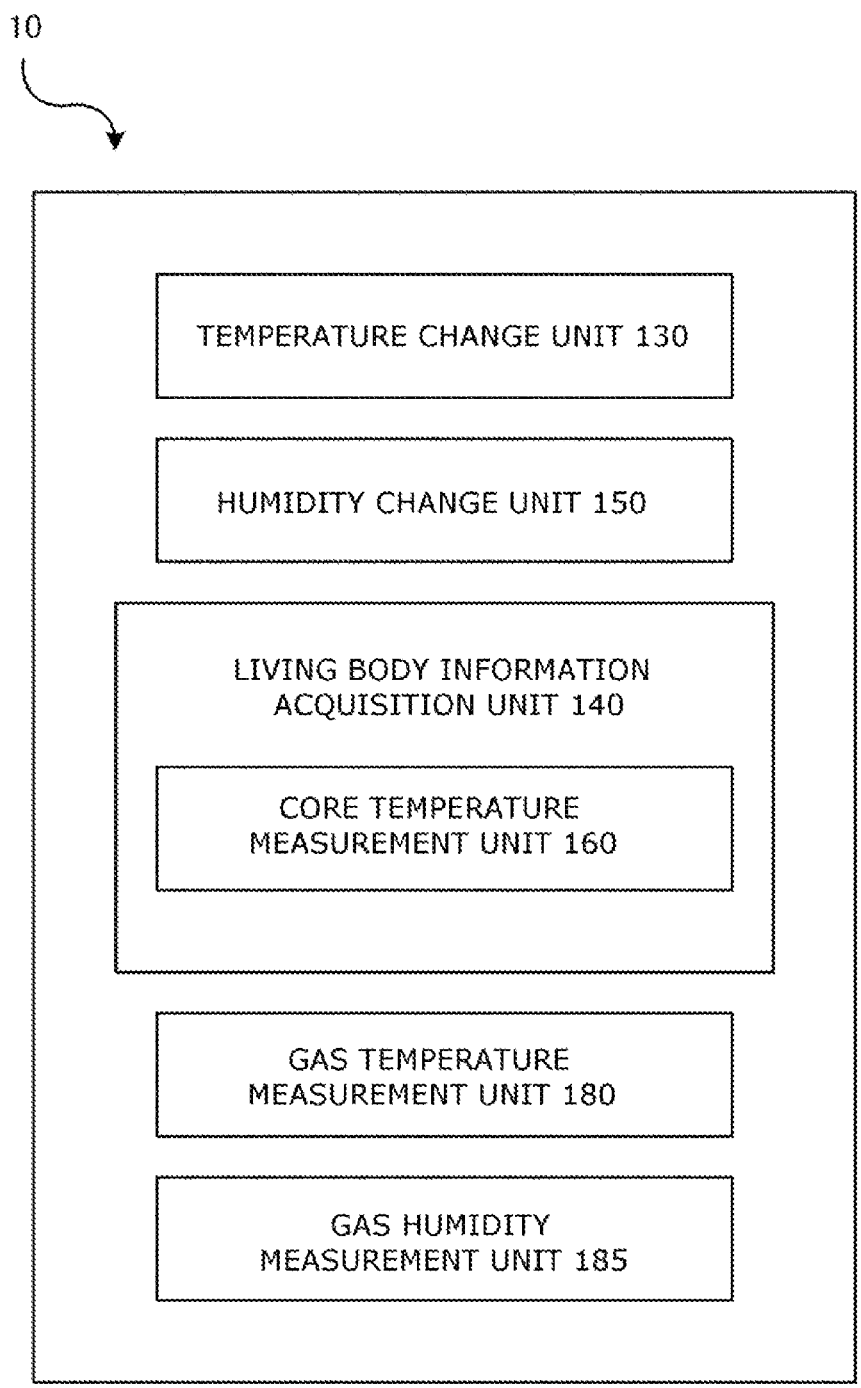
FIG. 5 is a block diagram of a control device that controls the respiratory assistance device.
Figure 6:
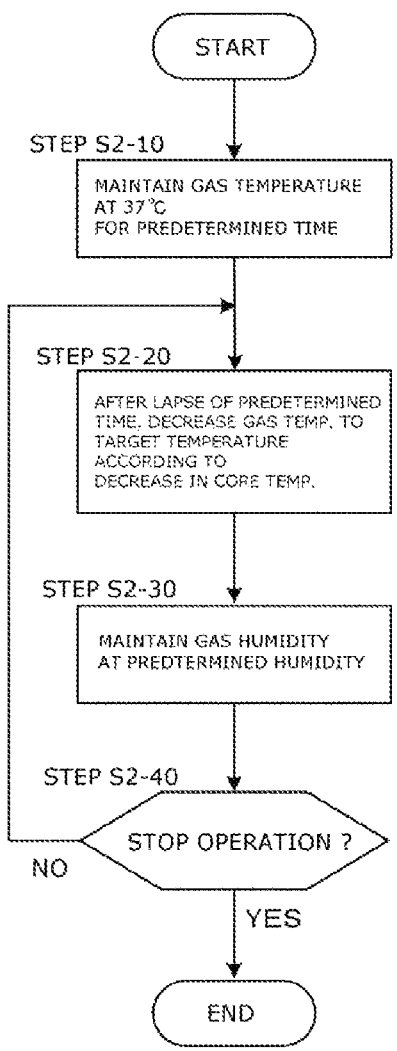
FIG. 6 is a flowchart about temperature control and humidity control on a blown gas.
Figure 6:
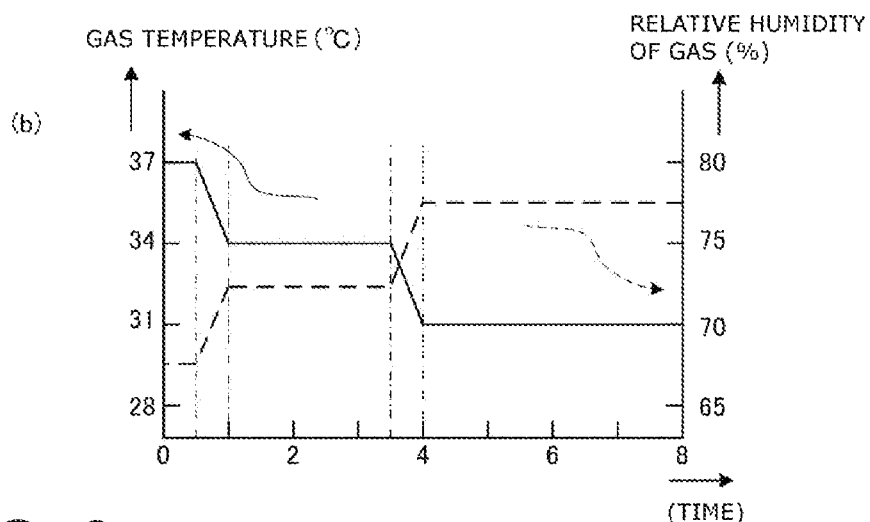

FIG. 5 shows a block diagram of the control device 10 in the respiratory assistance device 1 according to the second embodiment of the present invention. The control device 10 further includes a humidity change unit 150 which changes the gas humidity to a predetermined humidity and a gas humidity measurement unit 185 which measures the gas humidity in addition to the control device 10 according to the first embodiment.

Specifically, the respiratory circuit 70 of the respiratory assistance device 1 includes the gas humidity sensor 95 which detects the humidity of the gas, and the control device 10 includes the gas humidity measurement unit 185 which measures the gas humidity (see FIG. 4). The control device 10 further includes the humidity change unit 150 which changes the gas humidity to the predetermined humidity. The humidity change unit 150 controls the humidity adjustment unit 65. The gas humidity sensor 95 is connected to the gas humidity measurement unit 185. The humidity change unit 150 desirably performs feedback control on the gas humidity on the basis of the measured gas humidity.

FIG. 6(a) shows a flowchart about control that the control device 10 performs on the gas temperature and the gas humidity. A difference from the first embodiment shown in FIG. 3A is that the humidity change unit 150 of the control device 10, in (step S2-20), performs an operation for decreasing the gas temperature to the target temperature according to a decrease in the core temperature after a lapse of a predetermined time, and then in (step S2-30), performs an operation for maintaining the gas humidity to a predetermined humidity. The order may be reversed. (Step S2-30) may be performed simultaneously with or before and after (step S2-10).

While a mode of maintaining constant humidity has been described here, the humidifying device 50 may be controlled to change the gas humidity on the basis of the living body information to improve the comfort of the user. Specifically, the relative humidity may be increased or decreased according to a change in the core temperature. For example, when the core temperature decreases, there can be a lot of sweating to release heat from the body surface. The humidity change unit 150 then may perform control to set the target humidity high to prevent excessive loss of moisture from the body (see FIG. 6(b)). Conversely, when the core temperature increases, the humidity may be lowered.

The humidifying device 50 may be controlled to supply a predetermined amount of water vapor on the basis of a correlation between the gas humidity and the above-described gas temperature.

Figure 7:
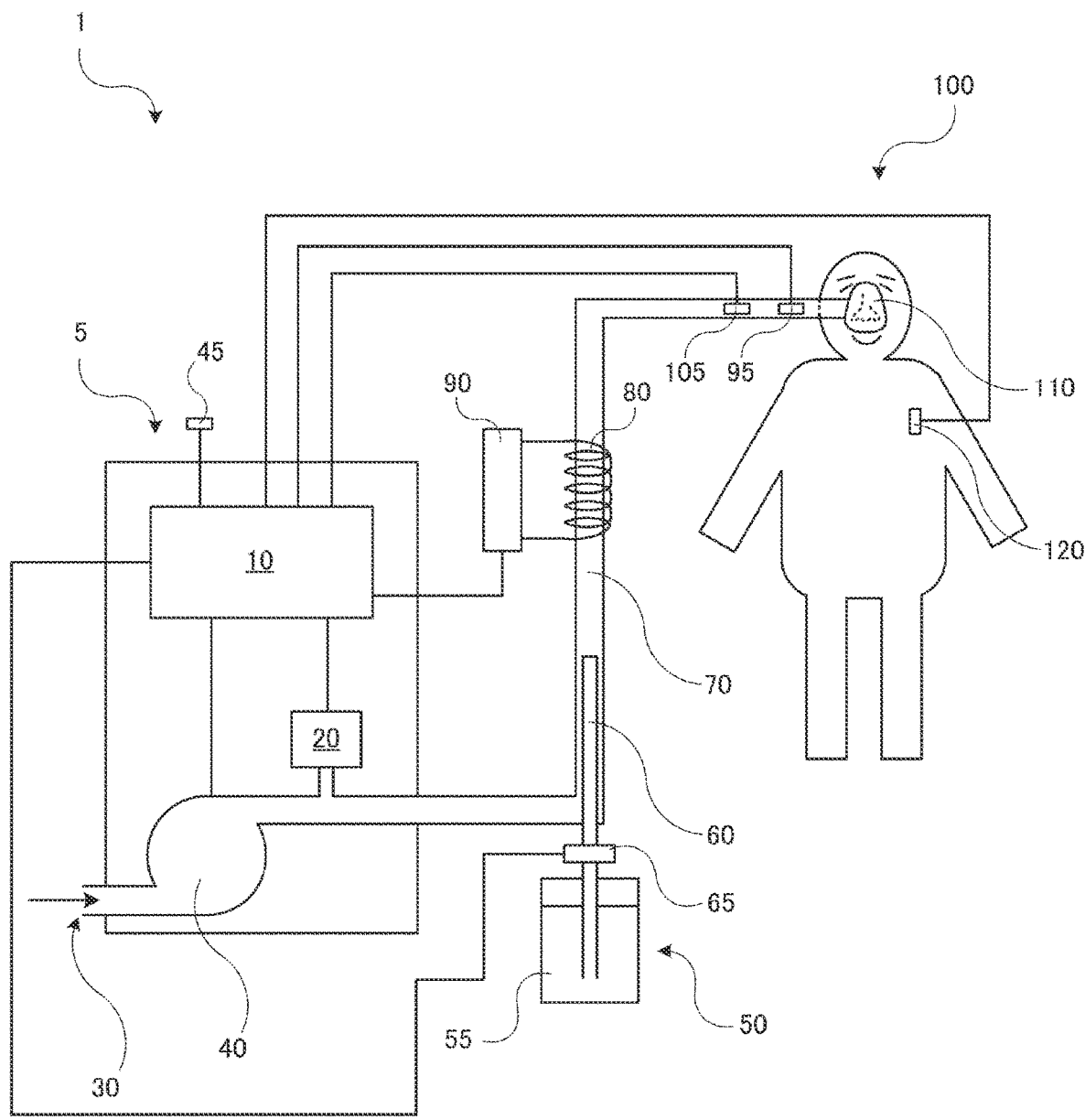
FIG. 7 is an explanatory diagram of a respiratory assistance device according to a third embodiment of the present invention.

FIG. 7 shows an explanatory diagram of a respiratory assistance device 1 according to a third embodiment of the present invention. A difference from the second embodiment lies in an outside air temperature measurement sensor 45 which detects an outside air temperature Tout (in units of degrees Celsius: ° C.) that is the temperature of the place where the user is.

Figure 8:
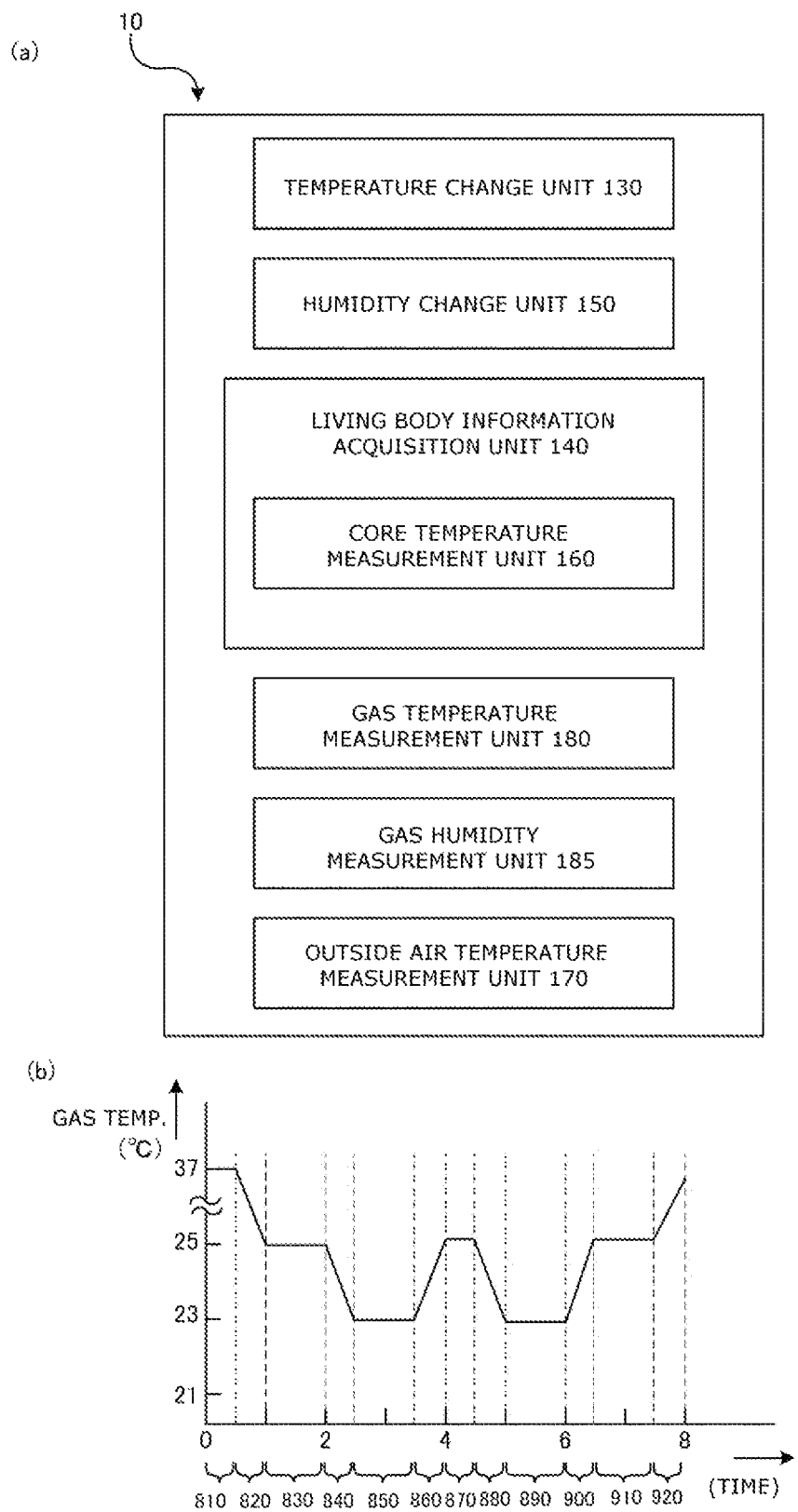
FIG. 8(a) is a block diagram of a control device that controls the respiratory assistance device.
FIG. 8(b) is a graph showing an example of gas temperature control.

FIG. 8(*a*) shows a block diagram of the control device 10 in the respiratory assistance device 1 according to the third embodiment. The control device 10 further includes an outside air temperature measurement unit 170 which is connected to the outside air temperature measurement sensor 45 and measures the outside air temperature. The temperature change unit 130 controls the gas temperature between (Tout-1) ° C. and (Tout-3) ° C. as a target temperature.

As described above, in a conventional respiratory assistance device used for respiratory assistance, the temperature of the blown gas is maintained at 37° C. The core temperature decreases during the onset of sleep. Conversely, decreasing the core temperature facilitates the onset of sleep. For the sake of the user's comfortable sleep, the gas temperature of the gas blown from the respiratory assistance device 1 is considered desirable to be the same temperature as the outside air temperature or a temperature, for example, approximately 1° C. to 3° C. lower than the outside air temperature Tout.

FIG. 8(*b*) shows a case where the core temperature is measured, the target temperature is changed according to a change in the core temperature, and the temperature change unit 130 performs temperature control to change the gas temperature. In the present modified example, the gas is blown at a temperature lower than the outside air temperature. Specifically, for example, suppose that the outside air temperature measured by the outside air temperature measurement unit 170 is constantly 25° C. Like the above-described modified examples, the gas temperature is maintained at 37° C. for the first 30 minutes. In the subsequent period 820, the gas temperature is lowered according to a decrease in the core temperature. In a period 830, the gas temperature is maintained since the core temperature does not change. In the subsequent period 840, the gas temperature is lowered again according to a decrease in the core temperature. The gas temperature is maintained at 23° C. that is 2° C. lower than the outside air temperature for the next one hour, since the core temperature does not change (period 850). In the subsequent period 860, the gas temperature is increased by 2° C. according to an increase in the core temperature. Subsequently, the gas temperature is similarly controlled according to a change in the core temperature. The gas temperature may be determined by also taking into account a change in the outside air temperature. Such a control on the gas temperature enables respiratory assistance comfortable to the user.

The cooling mechanism for making the temperature of the gas lower than the outside air temperature may be one commonly used for gas cooling. Like an ordinary refrigerator, a refrigerant and a compressor may be used to draw the heat of vaporization from the gas for cooling. A Peltier device may be used. It will be understood that the humidifying device 50 itself can be used for cooling. The gas temperature may be controlled to change according to a change in the core temperature.

The respiratory assistance device according to the present invention is not limited to the above-described embodiments, and various modifications may be made without departing from the gist of the present invention.

Figure 9:
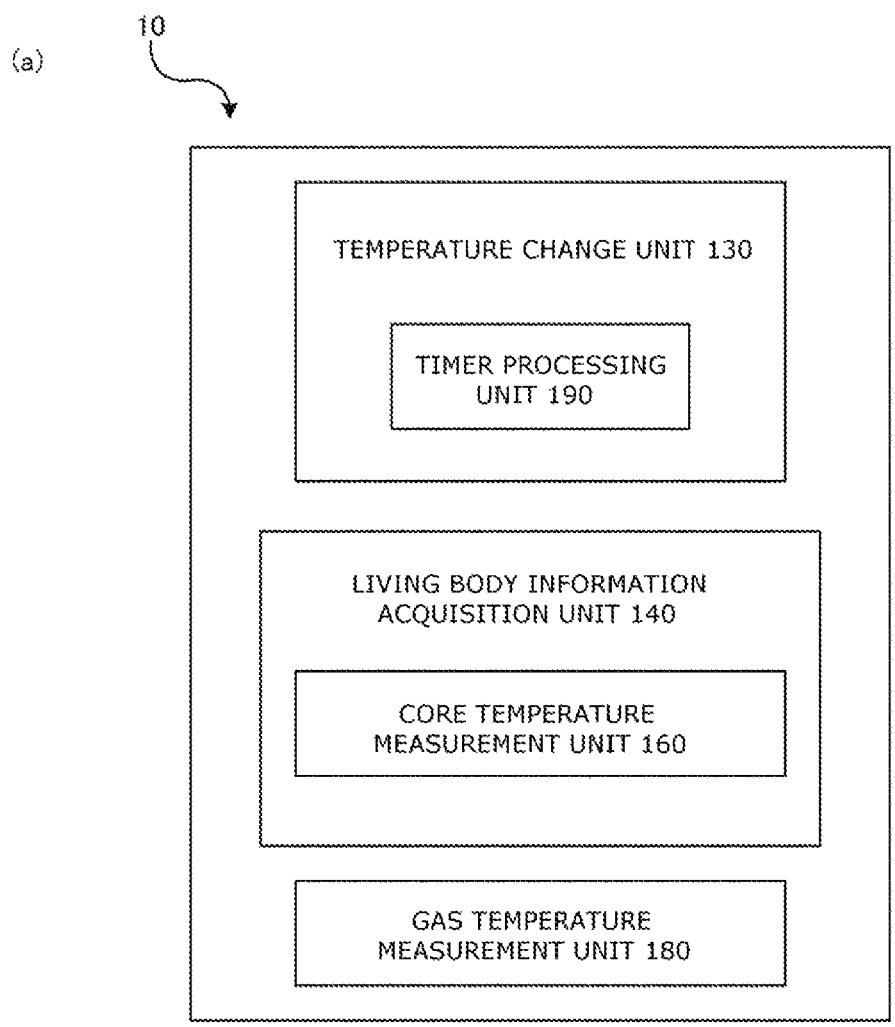
FIG. 9 is a block diagram of a control device according to a modified example.
Figure 9:
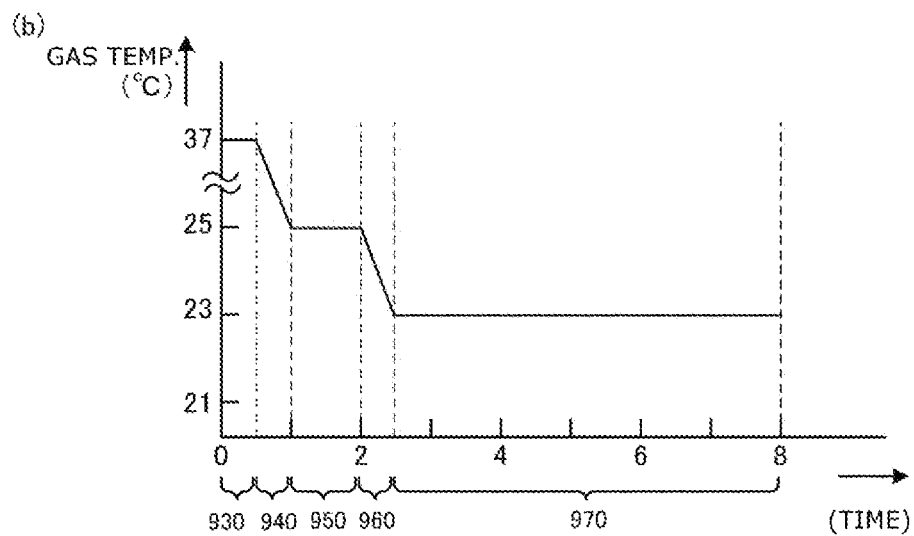

For example, in a modified example, as shown in FIG. 9(*a*), the temperature change unit 130 included in the respiratory assistance device 1 may include a timer processing unit 190. The timer processing unit 190 controls the gas temperature according to a lapse of time.

FIG. 9(*b*) shows an example where the timer processing unit 190 changes the gas temperature. For 30 minutes from the start of operation, the temperature change unit 130 maintains the gas temperature at 37° C. which is slightly higher than the body temperature (period 930). Recognizing the lapse of 30 minutes, the timer processing unit 190 then makes the temperature change unit 130 to decrease the gas temperature to 25° C. over 30 minutes (period 940). Recognizing the lapse of the period 940, the timer processing unit 190 then controls the warming unit 80 to maintain the gas temperature at 25° C. for the next one hour (period 950). The timer processing unit 190 subsequently makes similar operations, whereby the gas temperature is temperature-controlled according to the lapse of time. This provides the effect that the user can receive CPAP treatment both comfortably and effectively.

The respiratory assistance device 1 may have a plurality of operation modes, such as a timer mode in which the gas temperature is controlled according to a lapse of time as described above and a living body information mode in which the gas temperature is changed on the basis of the living body information, and may have a selection processing function by which the user can select one of the plurality of operation modes. The timer mode may be provided with a plurality of preset sequences, such as a sequence for decreasing the gas temperature at a constant rate over eight hours, aside from the sequence shown in FIG. 9(*b*), and the user may be allowed to select one.

For example, in modified examples of the second embodiment and the third embodiment, the humidity change unit 150 may include the timer processing unit 190 (see FIGS. 5 and 8). The timer processing unit 190 controls the gas humidity according to a lapse of time.

Figure 10:
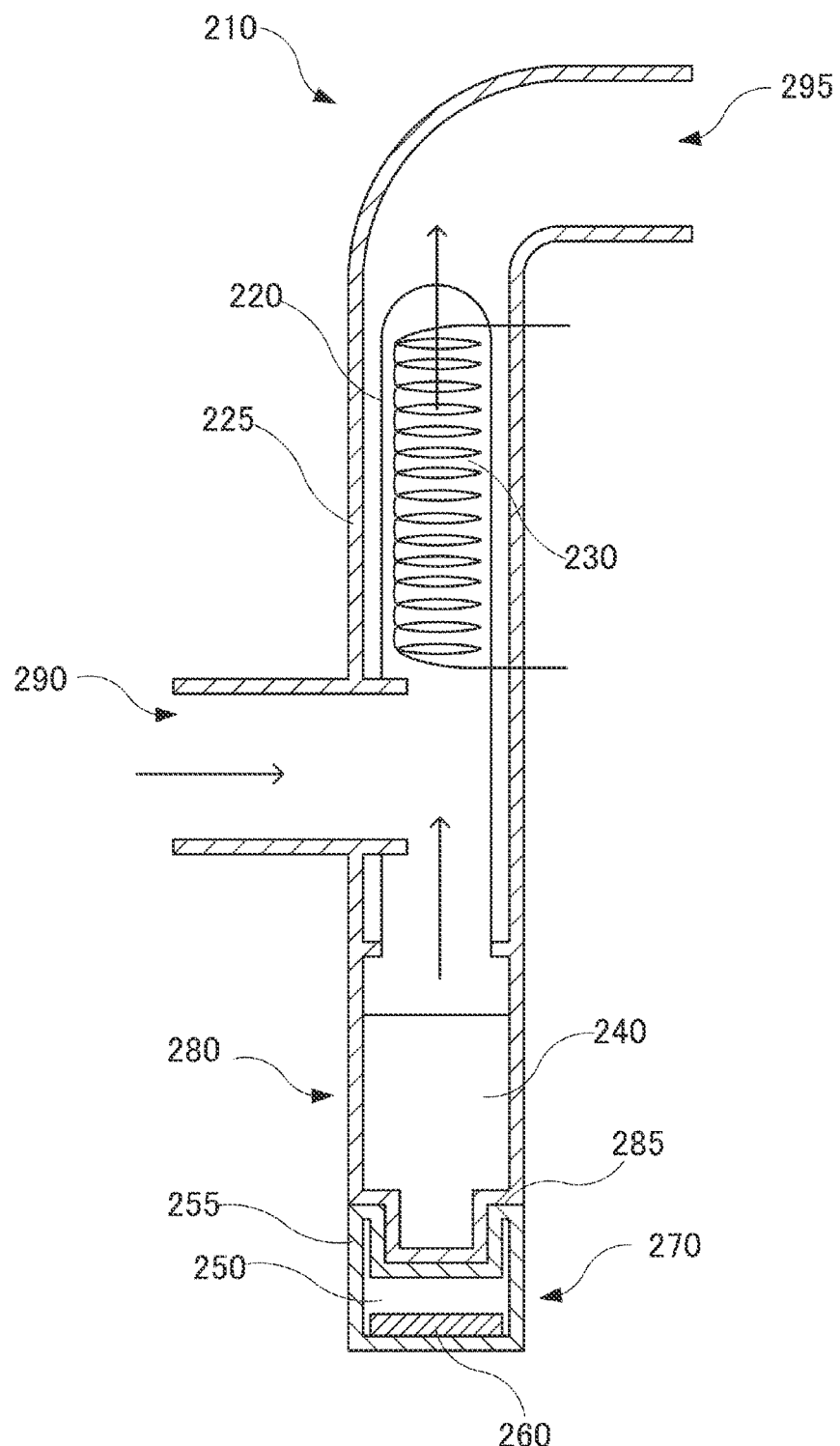
FIG. 10 is a cross-sectional view of a humidifying device according to a modified example.
Figure 11:
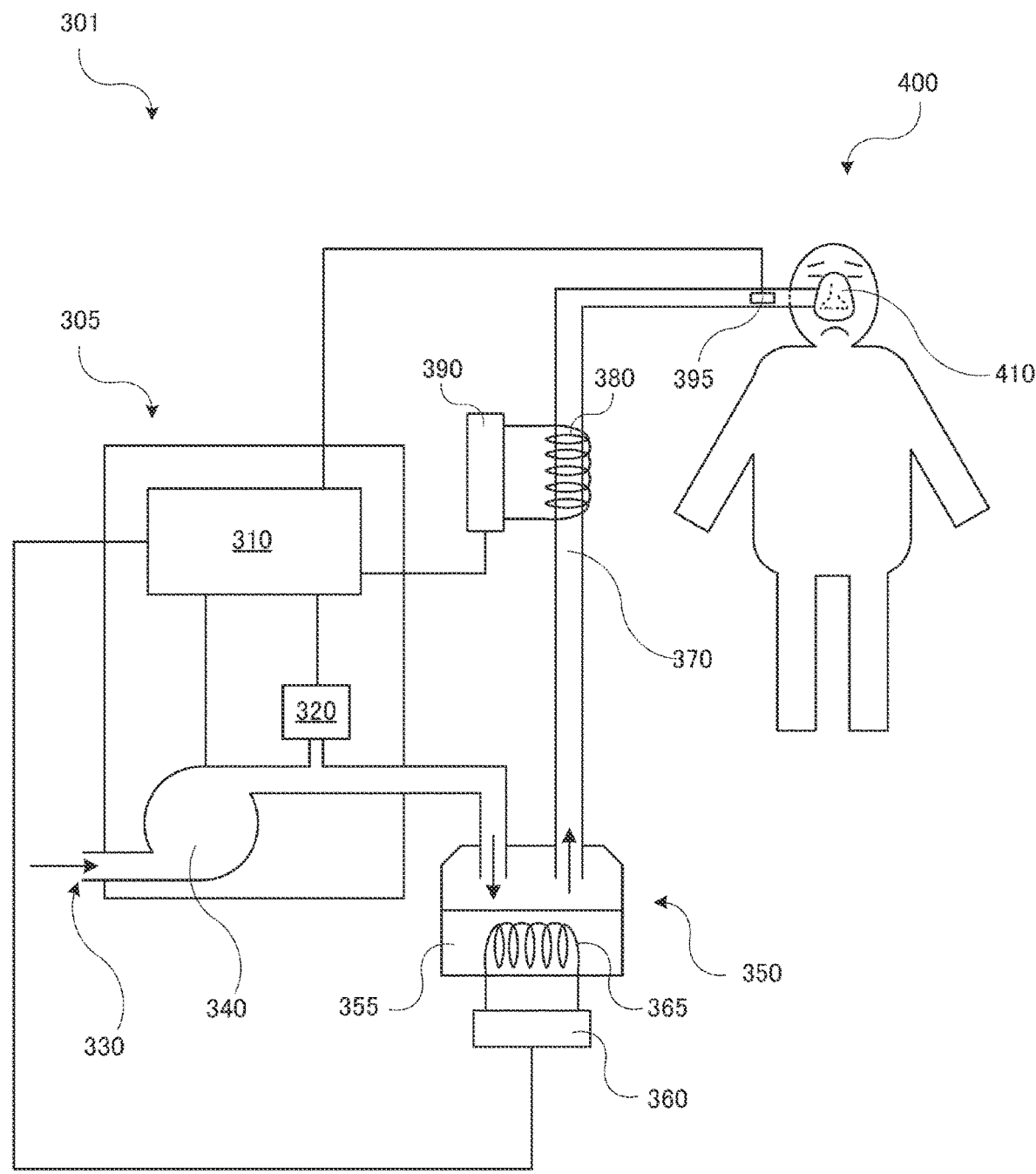
FIG. 11 is an explanatory diagram of a conventional respiratory assistance device.

For example, the humidifying device may be a conventional humidifying device of tank type or of a type shown in the next FIG. 10. FIG. 10 is a cross-sectional view of a humidifying device 210 according to a modified example of the present invention. Like a conventional humidifying device, the humidifying device 210 is connected to the respiratory circuit 70 of the respiratory assistance device for adjusting or assisting ventilation in the user's respiratory system, and gives the blown gas moisture in the form of fine particles or vapor of water. The humidifying device 210 includes a liquid container 280 which is arranged between a blower side pipe 290 and a respiratory circuit side pipe 295 and accommodates a liquid including at least water, a mist droplet generation unit 270 which generates mist droplets that are fine droplets of the liquid, and a water retaining member 220 which retains at least part of the mist droplets. In the present modified example, the mist droplet generation unit 270 generates mist droplets by ultrasonic vibrations as will be described later.

The mist droplet generation unit 270 includes an ultrasonic wave generation unit that vibrates the liquid to generate mist droplets. More specifically, in the humidifying device according to the present modified example, the mist droplet generation unit 270 is an ultrasonic mist droplet generation unit using a so-called cavitation effect of generating air bubbles on a liquid surface by using vibration energy from an ultrasonic vibrator. The mist droplet generation unit 270 includes a casing 255, an ultrasonic vibrator 260, and an ultrasonic transmission substance 250. An example of the ultrasonic transmission substance 250 is water. The water that is the ultrasonic transmission substance 250 retained in the casing 255 has high specific heat and is thus less prone to temperature increase, along with water 240 being in contact therewith via the casing 255 and a casing 225. The entire humidifying device 210 is thus suitable for long time use. The mist droplet generation unit 270 and the liquid container 280 are put in close contact with each other across a substance that easily transmits ultrasonic waves, such as a nonvolatile oil, at an interface 285.

The ultrasonic vibrator 260 is controlled by a controller (not shown) included in the control device 210. The controller includes a CPU, a RAM, a ROM, and the like for controlling the entire humidifying device 10. The CPU is a so-called central processing unit, and implements various functions by executing various programs. The RAM is used as a work area and storage area of the CPU. The ROM stores an operating system and programs to be executed by the CPU. The controller desirably has a function of monitoring the core temperature, the gas temperature, gas flow rate, and the like, and performing feedback control (such as PID control) on a heater and the like of a mist droplet heating unit 230 to make adjustments for a predetermined temperature and humidity. A warning is desirably issued if the water 240 in the liquid container 280 falls to or below a predetermined water level.

The amount of mist droplets generated by the mist droplet generation unit 270 is controlled by the controller. For example, if the amplitude of an alternating-current voltage applied to the ultrasonic vibrator 260 is increased, the amplitude of vibrations of the ultrasonic vibrator 260 increases and the amount of generated mist droplets increases. The liquid container 280 is desirably detachable from the casing 225. The mist droplet generation unit 270 is also desirably detachable from the liquid container 280.

The humidifying device 210 includes a flow path through which the blown gas flows. The flow path is closed by the water retaining member 220, and separated by the water retaining member 220 into an upstream side that is the blower 40 side where the liquid container 280 and the mist droplet generation unit 270 are arranged and a downstream side that is the user side. Specifically, the water retaining member 220 is cylindrical in shape and has a closed bottom. The open-side end of the cylinder is joined to the inner periphery of the casing 225, whereby the flow path is blocked. To reduce resistance to the gas passing through the water retaining member 220, an air passing area is desirably increased. For that purpose, spacers are desirably installed to leave a gap between the water retaining member 220 of cylindrical shape and the inner periphery of the casing 225. Instead of installing the spacers, the cylindrical diameter of the water retaining member 220 may be made sufficiently smaller than the inner peripheral diameter of the casing 225 to ensure the gap. The water retaining member 220 is water-absorbing unwoven fabric and desirably replaceable. Examples of the material of the unwoven fabric constituting the water retaining member 220 include polypropylene. For improved hydrophilicity, a surfactant treatment, a fluorine gas treatment, a sulfonation treatment, an acrylic acid grafting treatment, a plasma discharge treatment, or the like is desirably applied.

The water retaining member 220 is installed in the casing 225. The mist droplet heating unit 230 for heating and vaporizing mist droplets into water vapor is installed inside the water retaining member 220, i.e., on the liquid container 280 side. An example of the mist droplet heating unit 230 is a resistive heater made of a Nichrome wire or the like. A power supply (not shown) is connected to the mist droplet heating unit 230, and the controller controls power for temperature and humidity control on the basis of the gas temperature and the like. The water retaining member 220 cuts off mist droplets, but the gas containing the water vapor can pass through the water retaining member 220.

Next, an operation of the humidifying device according to the above-described modified example will be described, also with reference to FIG. 10.

A dry gas is supplied from the blower side pipe 290 to the humidifying device 210. The role of the humidifying device 210 is to give moisture to the gas. The humidification is performed by the following two methods.

(1) Mist droplets occurring from the surface of the liquid container 280 are vaporized into water vapor by the mist droplet heating unit 230. Vibration energy of the ultrasonic waves occurring from the ultrasonic vibrator 260 propagates to the water surface in the liquid container 280 and weakens the surface tension in part of the water surface, whereby fine mist droplets are generated. Being fine droplets, mist droplets have large surface areas relative to volume and are easy to vaporize. If mist droplets reach near the mist droplet heating unit 230, the mist droplets become even easier to vaporize due to high temperature and high saturated vapor pressure. The water vapor resulting from the vaporization consequently humidifies the dry gas.

(2) If mist droplets occurring from the surface of the liquid container 280 reach the water retaining member 220, the mist droplets adhere to the water retaining member 220. Since the water retaining member 220 has a water absorbing property, the moisture adhering to the water retaining member is retained as liquid water. When the gas blown from the blower side pipe 290 passes near the water retaining member 220, the moisture retained by the water retaining member 220 further increases the water vapor pressure of the blown gas for humidification.

The humidifying device 210 according to the modified example described above can generate water vapor for humidification with a smaller amount of energy than by ordinary boiling-based vaporization. Since a large amount of water vapor can be generated without boiling the stored water 240, there is provided an excellent effect that humidity can be controlled independent of temperature without excessively increasing the gas temperature. Since the blown gas is filtered through the water retaining member 220, there is also provided an effect that the water retaining member 220 also plays the role of a bacteria filter along with humidification.

Figure 12:
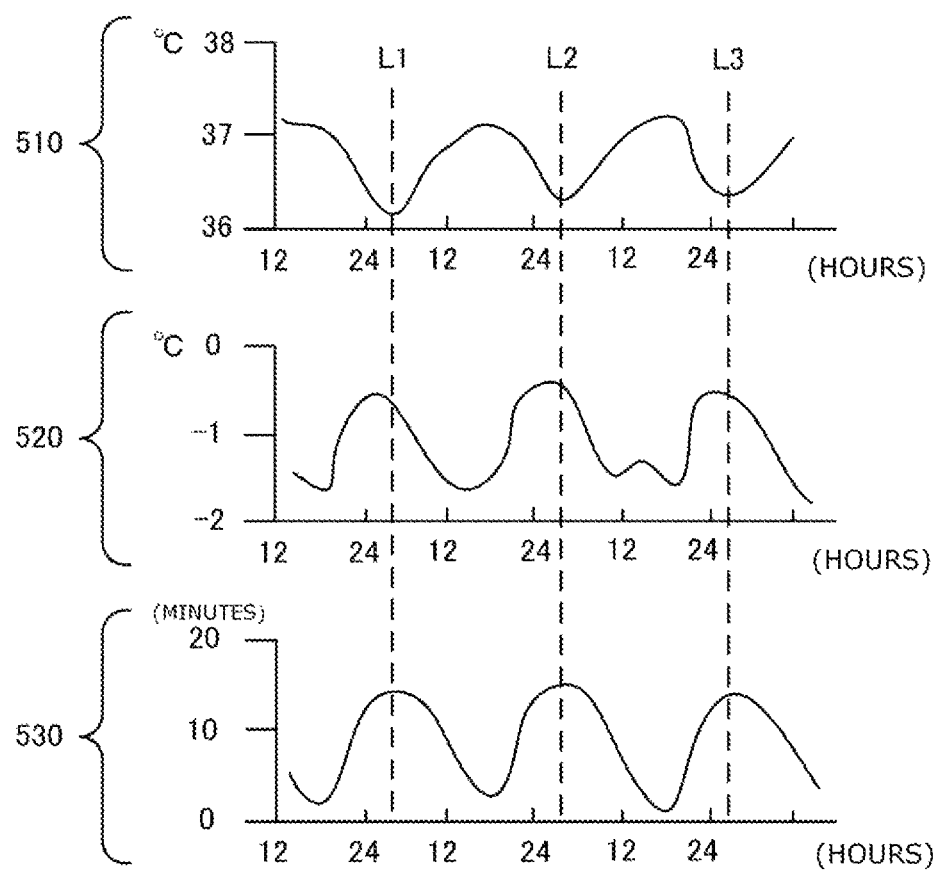
FIG. 12 shows graphs representing a relationship between time and a core temperature (region 510), the time and a relative temperature of the back of the hands and feet to the body (region 520), and the time and ease of sleep (region 530), respectively.

In another modified example, the gas temperature can be changed on the basis of a body surface temperature instead of the gas temperature being changed on the basis of the core temperature. Region 520 in FIG. 12 is a graph showing a relationship between time and a "relative temperature of the back of the hands and feet to the body." The "relative temperature of the back of the hands and feet to the body" is defined as a value determined by subtracting the skin temperature under the collarbone near the base of the neck (close to the abdomen or body core temperature) from the skin temperature at the back of the hands and feet. If the body surface temperature is represented by the above-described "relative temperature of the back of the hands and feet to the body," a comparison between Region 520 and 530 in FIG. 12 shows that there is a correlation between the body surface temperature and the ease of sleep. Specifically, the higher the body surface temperature, the higher the ease of sleep. Conversely, the lower the body surface temperature, the lower the ease of sleep. This is considered to reflect the fact that the human body increases the release of heat from the skin to decrease the core temperature, and suppresses the release of heat from the skin to increase the core temperature. In such a mode, the body surface temperature can be measured to implement a respiratory assistance device capable of controlling the gas temperature on the basis of a change in the core temperature without preparing a special core temperature sensor. This provides the effect of enabling more comfortable sleep under respiratory assistance.

Specifically, in a desirable configuration, the core temperature sensor 120 in FIG. 1 is rephrased as a body surface temperature sensor, and the core temperature measurement unit 160 in FIG. 2 is rephrased as a body surface temperature measurement unit for measuring the body surface temperature that is the temperature at the body surface of the user. In other words, the living body information acquisition unit 140 includes the body surface temperature measurement unit for measuring the body surface temperature that is the temperature at the body surface of the user. The temperature change unit 130 controls the warming unit 80 to decrease the gas temperature when the body surface temperature measured by the body surface temperature measurement unit increases.

In another modified example, an acceleration sensor for detecting body movements of the user can be attached to the user to capture body movements, and the gas temperature can be changed on the basis of that information.

A person with large body movements during sleep is in a so-called light sleep, or "REM sleep" state. A person with small body movements is in a so-called deep sleep, or "non-REM sleep" state. The control device 10 of the respiratory assistance device 1 includes a body movement measurement unit that measures body movements from the information about the body movements detected by the acceleration sensor, and a sleep depth determination unit that determines the depth of sleep of the user from the body movements measured by the body movement measurement unit. The temperature change unit 130 can decrease the gas temperature when the depth of sleep increases.

The respiratory assistance device 1 in such a mode provides an extremely excellent effect of enabling more comfortable sleep under respiratory assistance.

It will be understood that each of the above-described modified examples is applicable to all the embodiments and modified examples described in the present description.

Figure 13:
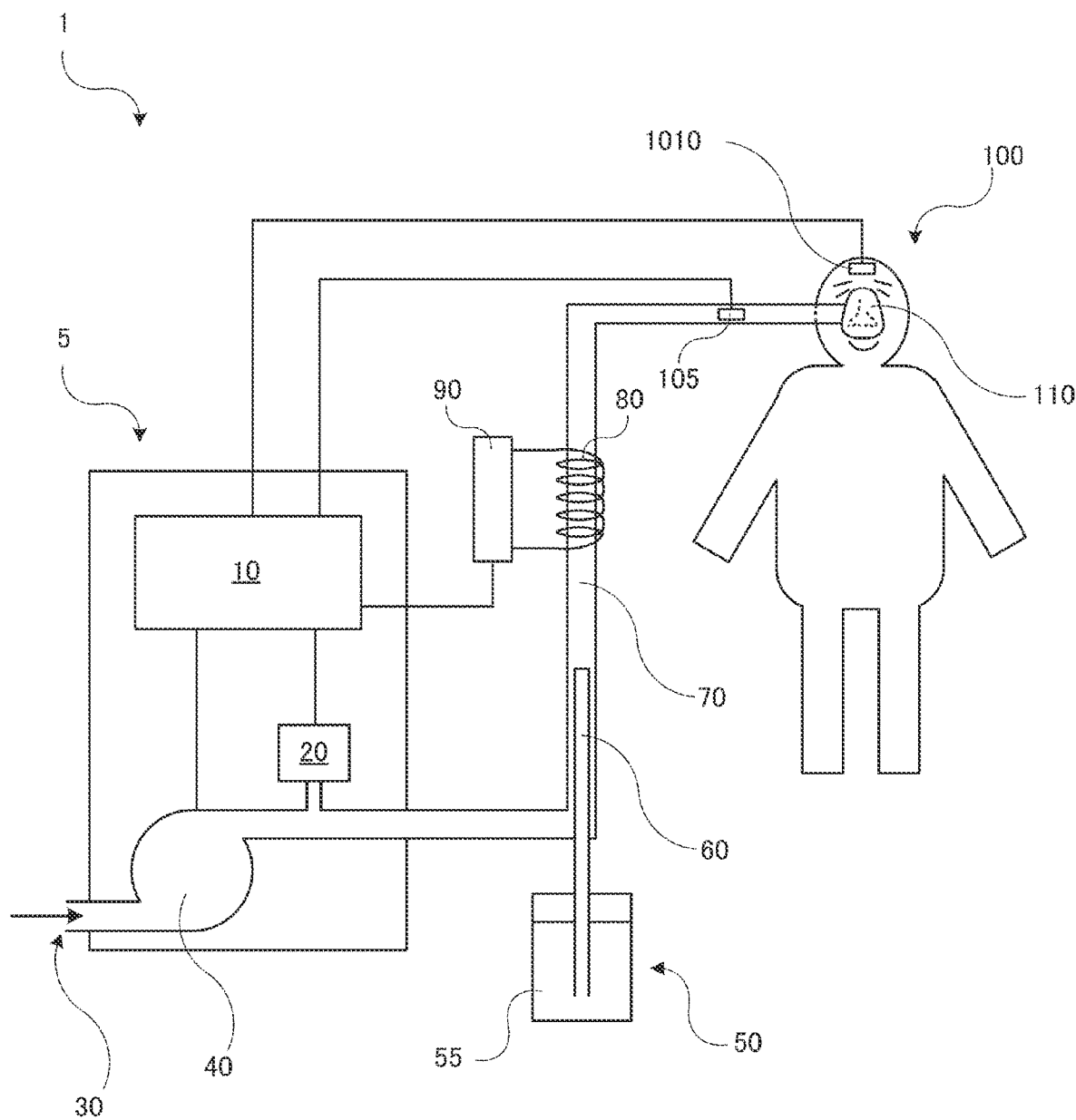
FIG. 13 is an explanatory diagram of a respiratory assistance device according to a fourth embodiment of the present invention.

FIG. 13 is an explanatory diagram for describing a respiratory assistance device 1 according to a fourth embodiment of the present invention. The respiratory assistance device 1 includes a control device 10 which controls the entire respiratory assistance device 1, and a main body 5 including a blower 40 which takes in a gas from an intake port 30 and sends out the gas to a user via a respiratory circuit 70. A flow rate measurement device 20 which measures the flow rate of the gas is provided on an outlet side of the blower 40. The respiratory assistance device 1 also includes a humidifying device 50 which moistens the blown gas. Water stored in a water storage unit 55 is transpired from a porous hollow fiber unit 60 to humidify the gas blown through the respiratory circuit 70.

Specifically, the respiratory assistance device 1 includes a respiratory interface device 110 which is worn by the user and delivers the gas, a gas temperature sensor 105 which measures a gas temperature that is the temperature of the gas, a warming unit 80 which warms the gas, a temperature change unit 130 (see FIG. 14 to be described later) which changes the gas temperature by controlling the warming unit 80, and a living body information acquisition unit 140 (see FIG. 14 to be described later) which obtains living body information about the user, or more specifically, a brain wave measurement unit 1010 which measures and obtains brain waves of the user. The temperature change unit 130 controls the warming unit 80 to change the gas temperature on the basis of the obtained brain waves. For example, the living body information acquisition unit 140 further includes a sleep level determination unit 1020 (see FIG. 14 to be described later) which determines a sleep level indicating the level of sleep of the user on the basis of the obtained living body information.

The brain wave measurement unit 1010 measures brain waves by using electrode probes attached to the user's head. This is a commonly well-known technique, and a detailed description thereof will thus be omitted.

The warming unit 80 is connected to a heater power supply 90. The heater power supply 90 is controlled by the control device 10, whereby the temperature of the gas is changed. For example, the control device 10 here desirably performs control to increase or decrease the temperature of the blown air to a predetermined temperature by feeding back the temperature measured by the gas temperature sensor 105.

In a modified example, the respiratory assistance device 1 may include a state determination unit that determines whether the user is in an awake state of being awake or in a sleep state of being asleep on the basis of the brain waves measured by the brain wave measurement unit 1010, for example. A brain wave determination unit that determines whether the user is in a REM sleep state or in a non-REM sleep state on the basis of the measured brain waves may be included. The temperature change unit 130 may control the warming unit 80 to increase or decrease the gas temperature on the basis of whether the user is in the REM sleep state or in the non-REM sleep state. Specifically, the temperature change unit 130 may control the warming unit 80 to decrease the gas temperature, for example, if the brain wave determination unit determines that the user is in the non-REM sleep state.

The brain wave determination unit may determine the depth of sleep of the user in more detail. Specifically, the brain wave determination unit may determine the degree of non-REM sleep of the user, such as the sleep stage of non-REM sleep. The temperature change unit 130 may control the warming unit 80 to increase or decrease the gas temperature on the basis of the degree of non-REM sleep.

Figure 14:
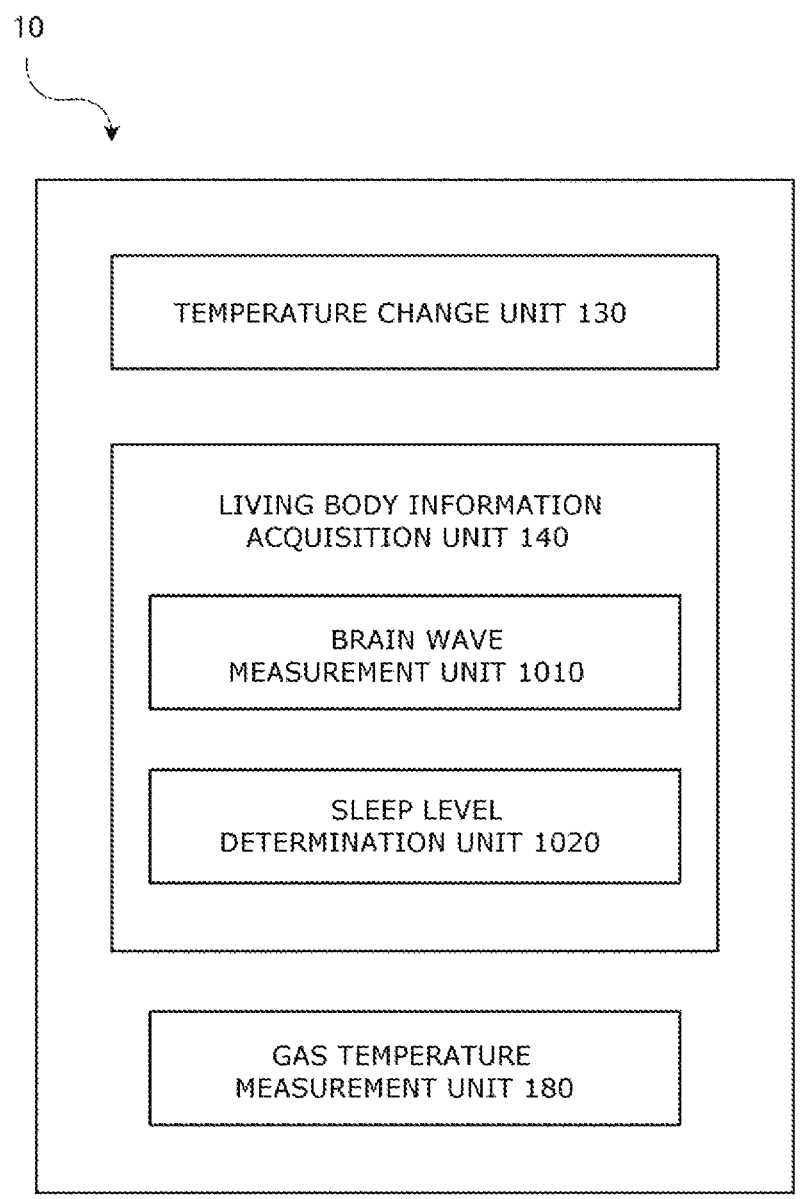
FIG. 14 is a block diagram of a control device that controls the respiratory assistance device.

FIG. 14 shows a block diagram of the control device 10 in the respiratory assistance device 1 according to the fourth embodiment of the present invention. The control device 10 includes the temperature change unit 130, the living body information acquisition unit 140, and a gas temperature measurement unit 180 which measures the temperature of the blown gas. The living body information acquisition unit 140 includes the brain wave measurement unit 1010 and the sleep level determination unit 1020 which determines the sleep level that is the level of sleep of the user on the basis of the brain waves measured by the brain wave measurement unit 1010. Specifically, sleep levels refer to sleep states typically classified by the waveform of the brain waves, namely, REM sleep and sleep stage 1 to sleep stage 4 of non-REM sleep (non-REM stage 1 to non-REM stage 4). The sleep levels may be divided between REM sleep and non-REM sleep, for example. Other classifications such as light sleep and deep sleep may be used.

If the user (measurement subject) is determined to be in an awake state from the waveform of the brain waves, the sleep level determination unit 1020 does not determine the sleep level.

The gas temperature measurement unit 180 measures and obtains the temperature of the gas, for example, by using the gas temperature sensor 105 (see FIG. 13). The control device 10 then controls the power output to the heater included in the warming unit 80 by controlling the heater power supply 90 by PID control, for example.

Figure 15:
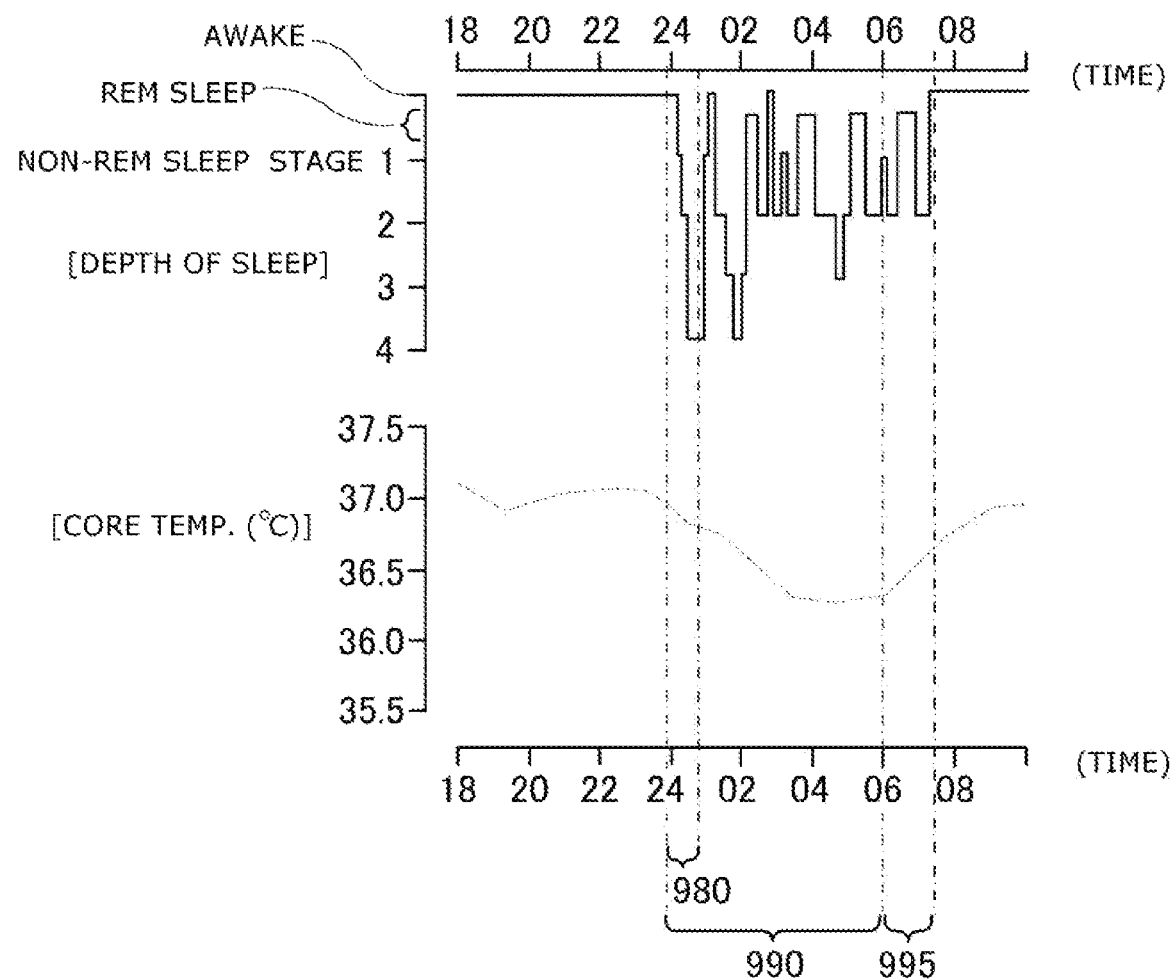
FIG. 15 is an explanatory diagram about a correlation between the depth of sleep and the core temperature.

FIG. 15 shows an explanatory diagram about a correlation between the depth of sleep and the core temperature. Specifically, FIG. 15 shows an example indicating the depth of sleep defined on the basis of the waveform of brain waves and how the core temperature changes according to a lapse of time from when a person in an awake state enters a sleep onset state to when the person wakes up. The horizontal axis of FIG. 15 indicates time. The upper solid line represents the depth of sleep, and the lower broken line represents the core temperature. Specifically, sleep levels are defined on the basis of the waveform of the brain waves of the user, and classified into REM sleep and sleep stage 1 to sleep stage 4 of non-REM sleep (non-REM stage 1 to non-REM stage 4). In a sleep onset region 980, the sleep level of the subject of the measurement shifts to non-REM sleep via REM sleep, and the depth of sleep increases from stage 1 to stage 4 of non-REM sleep. The sleep level then shifts to REM sleep and shifts to non-REM sleep again. In a sleep region 990 where non-REM sleep and REM sleep are thus repeated several times, the core temperature indicated by the broken line decreases. In an awakening region 995 where the sleep level shifts to an awake state via the last REM sleep, the core temperature increases.

Such a natural change in the core temperature can be interfered to lower the quality of sleep and impair the comfort of the user if the respiratory assistance device 1 blows, for example, a gas of constant temperature into the lungs which also play the role of, so to speak, a heat exchanger like a radiator in the human body. Conversely, the comfort of the user can be improved by changing the temperature of the gas blown by the respiratory assistance device 1 to not interfere with a natural change in the core temperature such as shown in FIG. 15.

If the sleep level is determined from the measured brain waves, the quality of the user's sleep can be improved by blowing a gas having a temperature likely to lower the core temperature, specifically, a gas having a temperature lower than the core temperature for, e.g., a certain time to facilitate a decrease in the core temperature.

Figure 16:
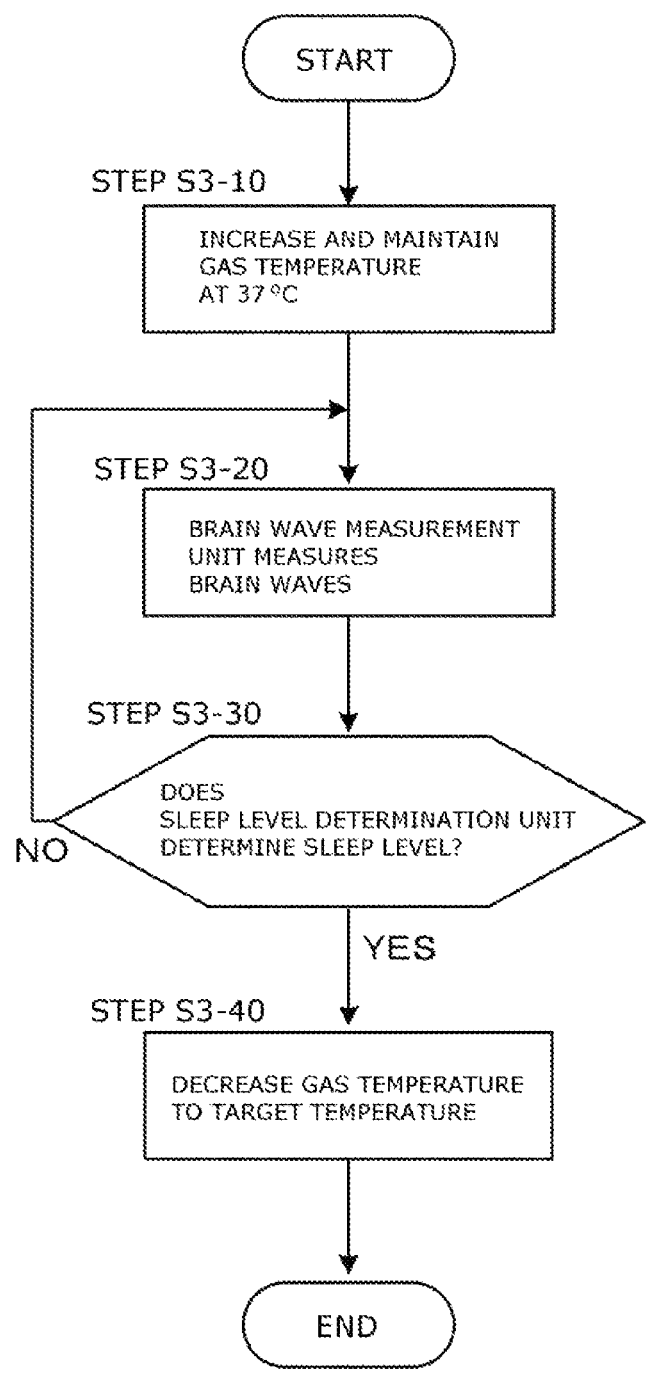
FIG. 16 is a flowchart about control for changing the temperature of the blown gas on the basis of brain waves.
Figure 17:
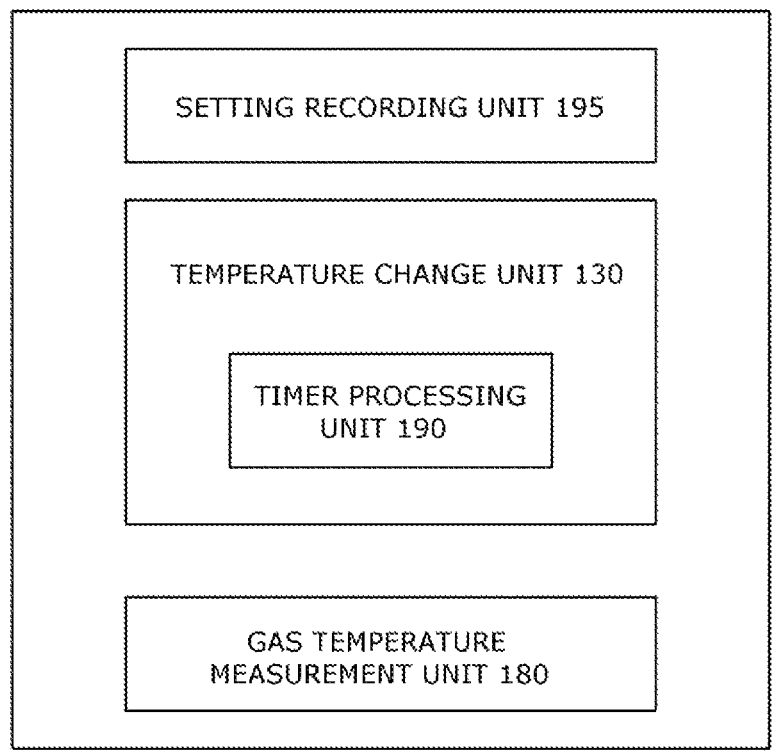
FIG. 17(a) is a block diagram of a control device that controls a respiratory assistance device according to a fifth embodiment of the present invention.
FIG. 17(b) is a graph showing a result of control in which the blown gas temperature is changed according to order and time intervals determined in advance.
Figure 17:
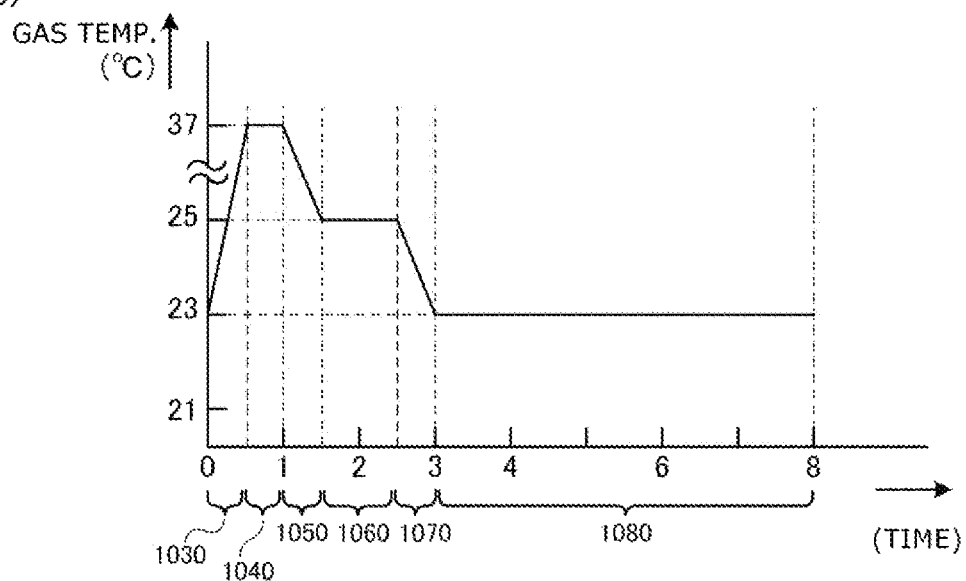

FIG. 16 shows a flowchart about control for changing the temperature of the blown gas on the basis of brain waves.

Initially, if the respiratory assistance device 1 is powered on, the blower 40 starts operation to start respiratory assistance (see FIG. 13). Although not shown in the drawings, setting values (such as a prescribed pressure) immediately before the previous power-off are automatically reflected upon power-on.

A timer function (not shown) for measuring the operation time from the start of operation is activated, and the gas temperature is increased to and maintained at a predetermined temperature, such as 37° C., for a predetermined time, such as 30 minutes (step S3-10). The reason is that blowing a relatively warm gas at the onset of sleep helps open the nasal cavity and is comfortable to the user. The predetermined time and the predetermined temperature are desirably adjustable as appropriate by the user.

The brain wave measurement unit 1010 measures the waveform of the brain waves (step S3-20). If the sleep level determination unit 1020 determines the sleep level of the user (YES in step S3-30), the control device 10, or the temperature change unit 130, decreases the gas temperature to a predetermined target temperature by controlling the heater power supply 90 to lower the temperature of the warming unit 80 (step S3-40). The target temperature is lower than the core temperature, and desirably the same as the outside air temperature or desirably 1° C. to 3° C. lower than the outside air temperature. If the target temperature is substantially the same as the outside air temperature, the temperature change unit 130 can reduce the power supplied to the heater power supply 90 or set the power to zero.

If the sleep level determination unit 1020 does not determine the sleep level of the user (NO in step S3-30), specifically, when the user is in an awake state, the control device 10 maintains the temperature of the gas at 37° C., for example.

The respiratory assistance device 1 according to the fourth embodiment of the present invention includes the living body information acquisition unit 140 which obtains the living body information about the user. The temperature of the blown gas can be changed on the basis of the obtained information. A gas having a temperature suitable for the user can thus be blown, with an excellent effect of improving the comfort of the user.

The respiratory assistance device 1 according to the fourth embodiment of the present invention includes the sleep level determination unit 1020 which determines the level of sleep of the user on the basis of the living body information obtained by the living body information acquisition unit 140. The temperature of the blown gas can thus be changed to a temperature suitable for the sleep level of the user, with an excellent effect of improving the comfort of the user.

In a modified example of the present invention, the respiratory assistance device 1 may include a state determination unit that determines whether the user is in an awake state of being awake or in a sleep state of being asleep on the basis of the brain waves measured by the brain wave measurement unit 1010. A brain wave determination unit that determines REM sleep and sleep stage 1 to sleep stage 4 of non-REM sleep (non-REM stage 1 to non-REM stage 4) may also be included, and the control device 10 may change the temperature of the blown gas by using the temperature change unit 130 on the basis of the determination. Specifically, the temperature of the blown gas is desirably changed to not interfere with a natural change in the core temperature such as shown in FIG. 15.

More specifically, if the brain wave determination unit that determines non-REM sleep and REM sleep is included and the brain wave determination unit determines that the measurement subject (user) is in the sleep region 990 (see FIG. 15) where non-REM sleep and REM sleep are repeated several times, the temperature of the blown gas is desirably decreased to not interfere with a decrease in the core temperature. Alternatively, a temperature lower than the minimum temperature of the core temperature may be maintained. If the temperature of the environment where the user sleeps is lower than the body surface temperature, a gas having the temperature of the environment where the user sleeps may continue to be blown.

The state determination unit and the brain wave determination unit may be included in the living body information acquisition unit 140 (see FIG. 14). The state determination unit and the brain wave determination unit may be integrated with the sleep level determination unit.

The human core temperature typically decreases in a sleep state. For example, continuing blowing a gas having a temperature higher than the body surface temperature then interferes with the decrease in the core temperature. This is unpleasant for the user and can sometimes lower the quality of sleep. According to a modified example of the present invention, the state determination unit that determines whether the user is in an awake state or in a sleep state on the basis of the brain waves is included. When the user enters a sleep state, the temperature of the blown gas can thus be changed to a temperature suitable for the sleep state. This provides an excellent effect that the comfort of the user improves.

Human sleep is classified into REM sleep and non-REM sleep on the basis of a difference in brain behavior. Sleep typically progresses from an onset to wake-up while repeating non-REM sleep and REM sleep alternately. The process of repetition and temporal changes in the core temperature correlate with each other. According to a modified example of the present invention, non-REM sleep and REM sleep can be determined from the measured brain waves, and the state of the core temperature can thus be estimated. This provides an excellent effect in that the temperature of the blown gas can be changed to a temperature suitable for the user.

It is known that the human core temperature decreases as the sleep shifts from the first REM sleep after onset to non-REM sleep, and the core temperature increases as the stage of non-REM sleep lightens. According to a modified example of the present invention, the change in the core temperature can be estimated on the basis of the brain waves. This provides an excellent effect that the comfort of the user can be improved since the temperature of the blown gas can be changed to not interfere with a natural change in the core temperature.

Sleep typically progresses from an onset to wake-up while repeating non-REM sleep and REM sleep alternately. The process of repetition and temporal changes in the core temperature correlate with each other. Specifically, it is known that the core temperature tends to decrease as the sleep stage of non-REM sleep deepens, and the core temperature decreases in each of several non-REM sleeps repeated before wake-up. According to a modified example of the present invention, if the brain wave determination unit determines that the user is in a non-REM sleep state, the temperature change unit 130 controls the warming unit 80 to decrease the gas temperature. This provides an excellent effect that the temperature of the gas can be changed to not interfere with a natural change in the core temperature.

The human core temperature tends to decrease when the degree of non-REM sleep, or more specifically, the sleep stage of non-REM sleep deepens, and be maintained when the degree of non-REM sleep lightens. According to a modified example of the present invention, the brain wave determination unit that can determine the degree of non-REM sleep is included. This provides an excellent effect that the temperature of the gas can be changed to not interfere with a natural change in the core temperature.

FIG. 17(a) shows a block diagram of a control device 10 that controls a respiratory assistance device 1 according to a fifth embodiment of the present invention.

The control device 10 includes a temperature change unit 130, a gas temperature measurement unit 180 which measures the temperature of a blown gas, and a setting recording unit 195 in which settings for changing the temperature of the gas according to predetermined order and time intervals are input and recorded. Specifically, the temperature change unit 130 includes a timer processing unit 190 which controls the gas temperature according to a lapse of time on the basis of the settings recorded in the setting recording unit 195. The temperature change unit 130 desirably performs feedback control on the temperature of the gas measured by the gas temperature measurement unit 180.

The rest of the configuration of the respiratory assistance device 1, except the brain wave measurement unit 1010, is the same as that of the fourth embodiment of the present invention. A description thereof will thus be omitted.

FIG. 17(b) shows a graph showing a result of control in which the blown gas temperature is changed according to predetermined order and time intervals. The temperature of the blown gas is controlled by the timer processing unit 190 included in the temperature change unit 130 on the basis of the settings recorded in the setting recording unit 195. Specifically, if, for example, the temperature of the environment where the user is 23° C., the timer processing unit 190 controls the gas temperature, including an increase region 1030 in which the temperature of the blown gas is increased to 37° C. over 30 minutes since the respiratory assistance device 1 has started operation. The timer processing unit 190 also controls the gas temperature, including a maintenance region 1040 in which the temperature of the gas is maintained for 30 minutes after the increase region. The timer processing unit 190 further controls the gas temperature, including a decrease region 1050 in which the temperature of the gas is decreased for 30 minutes after the maintenance region 1040. The timer processing unit 190 then controls the gas temperature so that a maintenance region 1060, a decrease region 1070, and a maintenance region 1080 are included.

In the respiratory assistance device 1 according to the fifth embodiment of the present invention, the temperature change unit 130 includes the timer processing unit 190 which controls the gas temperature according to a lapse of time. The gas temperature can thus be controlled according to a preset timer program. This facilitates providing the effect of improving the comfort of the user.

In blowing the gas through the nasal cavity, a gas temperature somewhat higher than the body surface temperature can help open the nasal cavity in an awake state. The respiratory assistance device 1 according to the fifth embodiment of the present invention maintains the temperature of the blown gas at or above the body surface temperature for an average time the user is considered to take from the start of operation of the device to the onset of sleep, such as 30 minutes. This provides an excellent effect that the nasal cavity can be opened to bring about a state in which the user can easily fall asleep.

The human core temperature changes with a lapse of time from the onset of sleep to wake-up. The respiratory assistance device 1 according to the firth embodiment of the present invention can change the temperature of the blown gas according to predetermined order and time intervals input in advance. This provides an excellent effect that the comfort of the user can be improved since the gas can be blown at optimum gas temperature according to expected temporal changes in the core temperature.

In a modified example of the present invention, for example, the timer processing unit 190 can perform control to stop the warming unit 80. The human core temperature typically decreases if an awake state shifts to a sleep state. Continuing blowing a gas having a temperature higher than the body surface temperature, for example, then interferes with the decrease in the core temperature. This is unpleasant for the user and can sometimes lower the quality of sleep. According to the modified example described above, the warming of the gas can be automatically stopped after a lapse of an average time that the user is considered to take from the start of operation of the device to the onset of sleep, such as 30 minutes. This provides an excellent effect that the comfort of the user can be improved since the temperature of the gas can be decreased at least to the room temperature to not interfere with a natural change in the core temperature.

In a modified example of the present invention, the timer processing unit 190 may perform control to bring the temperature of the gas to a temperature lower than or equal to the body surface temperature of the user. The human core temperature typically decreases if an awake state shifts to a sleep state. Continuing blowing a gas having a temperature higher than the body surface temperature, for example, then interferes with the decrease in the core temperature. This is unpleasant for the user and can sometimes lower the quality of sleep. According to the modified example described above, the temperature of the blown gas can be automatically made lower than the body surface temperature with a lapse of time. This provides an excellent effect that the comfort of the user can be improved since the temperature of the gas can be lowered at least to the room temperature to not interfere with a natural change in the core temperature.

In another modified example of the present invention, the timer processing unit 190 may control the temperature of the gas to a temperature higher than the melting point of water in the environment in which the respiratory assistance device 1 is run. The respiratory assistance device 1 is intended for a user who does not have much trouble other than in the respiratory system. Lowering the temperature of the blown gas more than needed rather impairs the comfort of the user. According to the modified example described above, the temperature of the blown gas is maintained at a temperature higher than the freezing point of water, or more specifically, the melting point of water in the environment in which the device is run. This provides an excellent effect that the comfort of the user is less likely to be impaired since an unnecessarily cold gas will not be blown.

In yet another modified example of the present invention, when the gas temperature is decreased or changed to a predetermined target temperature, the target temperature may be defined in various ways with reference to the outside air temperature or the body surface temperature. For example, if the target temperature of the gas temperature is defined with reference to an outside air temperature Tout (in units of degrees Celsius: ° C.) that is the temperature of the place where the user is, the target temperature may be (Tout-10) ° C. or higher and not higher than Tout. For example, if the target temperature of the gas temperature is defined with reference to the outside air temperature Tout, the target temperature may be (Tout-5) ° C. or higher and not higher than Tout. If the target temperature of the gas temperature is defined with reference to a body surface temperature Tbody (in units of degrees Celsius: ° C.), the target temperature may be (Tbody-10) ° C. or higher and not higher than Tbody. For example, if the target temperature of the gas temperature is defined with reference to the body surface temperature Tbody, the target temperature may be (Tbody-5) ° C. or higher and not higher than Tbody. It will be understood that the target temperature may be similarly defined with reference to the core temperature. For example, if the target temperature of the gas temperature is defined with reference to a core temperature Tdeep (in units of degrees Celsius: ° C.), the target temperature may be (Tdeep-10) ° C. or higher and not higher than Tdeep. For example, if the target temperature of the gas temperature is defined with reference to the core temperature Tdeep, the target temperature may be (Tdeep-5) ° C. or higher and not higher than Tdeep. Smaller temperature changes can sometimes be comfortable, and larger temperature changes conversely can sometimes be comfortable. In either case, various target temperatures are desirably selectable by the user.

It will be understood that each of the above-described modified examples is applicable to all the embodiments and modified examples described in the present description.

REFERENCE SIGNS LIST 1 respiratory assistance device
5 main body
10 control device
20 flow rate measurement device
30 intake port
40 blower
45 outside air temperature measurement sensor
50 humidifying device
55 water storage unit
60 porous hollow fiber unit
65 humidity adjustment unit
70 respiratory circuit
80 warming unit
90 heater power supply
95 gas humidity sensor
100 user
105 gas temperature sensor
110 respiratory interface device
120 core temperature measurement sensor
130 temperature change unit
140 living body information acquisition unit
150 humidity change unit
160 core temperature measurement unit
170 outside air temperature measurement unit
180 gas temperature measurement unit
185 gas humidity measurement unit
190 timer processing unit
195 setting recording unit
210 humidifying device
220 water retaining member
225 casing
230 mist droplet heating unit
240 water
250 ultrasonic transmission substance
255 casing
260 ultrasonic vibrator
270 mist droplet generation unit
280 liquid container
285 interface
290 blower side pipe
301 conventional respiratory assistance device 301
305 main body
310 control device
320 flow rate measurement device
330 intake port
340 blower
350 humidifying device
355 water storage unit
360 heater power supply
365 warming unit
370 respiratory circuit
380 warming unit
390 heater power supply
395 gas temperature sensor
400 user
410 respiratory interface device
1010 brain wave measurement unit
1020 sleep level determination unit

The invention claimed is:

1. A respiratory assistance device comprising:
a respiratory interface device configured to be worn by a user and deliver a gas;
a gas temperature measurement unit configured to measure a gas temperature that is a temperature of the gas;
a warming unit configured to warm the gas;
a temperature change unit configured to change the gas temperature by controlling the warming unit; and
an outside air temperature measurement unit configured to measure an outside air temperature that is a temperature of a place where the user is, wherein the temperature change unit controls the gas temperature on a basis of the outside air temperature;
wherein the outside air temperature is defined as Tout (in units of degrees Celsius), and the temperature change unit controls the gas temperature between (Tout-1) and (Tout-3).

2. The respiratory assistance device according to claim 1, further comprising a humidifying device configured to humidify the gas.

3. The respiratory assistance device according to claim 2, wherein
the humidifying device includes:
a water storage unit configured to store water intended for humidification; and
a porous hollow fiber unit to which the water in the water storage unit is supplied.

4. The respiratory assistance device according to claim 2, comprising:
a gas humidity measurement unit configured to measure a gas humidity that is a humidity of the gas; and
a humidity change unit configured to control the humidifying device to change the gas humidity to a predetermined humidity.

5. The respiratory assistance device according to claim 4, wherein the humidity change unit controls the humidifying device to supply a predetermined amount of water vapor on a basis of a correlation between the gas humidity and the gas temperature.

6. The respiratory assistance device according to claim 4, comprising a living body information acquisition unit configured to obtain living body information about the user, wherein
the humidity change unit controls the humidifying device to change the gas humidity on a basis of the living body information.

7. The respiratory assistance device according to claim 1, comprising a living body information acquisition unit configured to obtain living body information about the user, wherein
the temperature change unit controls the warming unit to change the gas temperature on a basis of the living body information.

8. The respiratory assistance device according to claim 7, wherein the living body information acquisition unit includes a core temperature measurement unit configured to measure a core temperature that is a temperature of a deep part of the user's living body.

9. The respiratory assistance device according to claim 8, wherein the temperature change unit controls the warming unit to decrease the gas temperature when the core temperature measured by the core temperature measurement unit decreases.

10. The respiratory assistance device according to claim 8, wherein the temperature change unit controls the gas temperature to or below the core temperature.

11. The respiratory assistance device according to claim 7, wherein the living body information acquisition unit includes a body surface temperature measurement unit configured to measure a body surface temperature that is a temperature of a body surface of the user.

12. The respiratory assistance device according to claim 11, wherein the temperature change unit controls the warming unit to decrease the gas temperature when the body surface temperature measured by the body surface temperature measurement unit increases.

13. The respiratory assistance device according to claim 7, wherein the living body information acquisition unit includes a body movement measurement unit configured to measure body movement of the user.

14. The respiratory assistance device according to claim 13, comprising a sleep depth determination unit configured to determine depth of sleep of the user from the body movement measured by the body movement measurement unit, wherein
the gas temperature is lowered when the depth of sleep increases.

15. The respiratory assistance device according to claim 7, further comprising a sleep level determination unit configured to determine a sleep level indicating a level of sleep of the user on a basis of the living body information obtained by the living body information acquisition unit, wherein
the temperature change unit controls the warming unit to change the gas temperature on a basis of the sleep level.

* * * * *